(12) United States Patent
Wallace et al.

(10) Patent No.: US 10,143,552 B2
(45) Date of Patent: Dec. 4, 2018

(54) REPLACEMENT MITRAL VALVES

(71) Applicant: CEPHEA VALVE TECHNOLOGIES, INC., San Jose, CA (US)

(72) Inventors: Dan Wallace, Santa Cruz, CA (US); Spencer Noe, Santa Cruz, CA (US); Peter Gregg, Santa Cruz, CA (US); Juan F. Granada, Upper Saddle River, NJ (US)

(73) Assignee: Cephea Valve Technologies, Inc., San Jose, CA (US)

( * ) Notice: Subject to any disclaimer, the term of this patent is extended or adjusted under 35 U.S.C. 154(b) by 0 days.

(21) Appl. No.: 15/669,805

(22) Filed: Aug. 4, 2017

(65) Prior Publication Data

US 2017/0325948 A1 Nov. 16, 2017

Related U.S. Application Data

(63) Continuation of application No. PCT/US2016/032550, filed on May 13, 2016.
(Continued)

(51) Int. Cl.
*A61F 2/24* (2006.01)
*A61F 2/82* (2013.01)

(52) U.S. Cl.
CPC .......... *A61F 2/2418* (2013.01); *A61F 2/2409* (2013.01); *A61F 2002/825* (2013.01); *A61F 2220/0008* (2013.01); *A61F 2230/0006* (2013.01); *A61F 2230/0013* (2013.01); *A61F 2230/0071* (2013.01);
(Continued)

(58) Field of Classification Search
CPC ................................................... A61F 2/2418
See application file for complete search history.

(56) References Cited

U.S. PATENT DOCUMENTS

| 3,334,629 A | 8/1967 | Cohn |
| 3,409,013 A | 11/1968 | Henry |

(Continued)

FOREIGN PATENT DOCUMENTS

| CA | 2859666 A1 * | 6/2013 | ............... A61F 2/24 |
| CN | 1338951 A | 3/2002 | |

(Continued)

OTHER PUBLICATIONS

Andersen et al.; Transluminal implantation of artificial heart valves. Description of a new expandable aortic valve and initial results with implantation by catheter technique in closed chest pigs; Euro. Heart J.; 13 (5): 704-708; May 1992.
(Continued)

*Primary Examiner* — Brian Pellegrino
(74) *Attorney, Agent, or Firm* — Shay Glenn LLP

(57) ABSTRACT

A prosthetic mitral valve includes an anchor assembly, an annular strut frame, and a plurality of replacement leaflets secured to the annular strut frame. The anchor assembly includes a ventricular anchor, an atrial anchor, and a central portion therebetween. The annular strut frame is disposed radially within the anchor assembly. An atrial end of the annular strut frame is attached to the anchor assembly such that a ventricular end of the annular strut frame is spaced away from the anchor assembly.

16 Claims, 34 Drawing Sheets

Related U.S. Application Data

(60) Provisional application No. 62/161,743, filed on May 14, 2015, provisional application No. 62/259,565, filed on Nov. 24, 2015.

(52) U.S. Cl.
CPC . *A61F 2250/006* (2013.01); *A61F 2250/0018* (2013.01); *A61F 2250/0069* (2013.01)

(56) References Cited

U.S. PATENT DOCUMENTS

| | | | |
|---|---|---|---|
| 3,540,431 A | 11/1970 | Mobin-Uddin | |
| 3,628,535 A | 12/1971 | Ostrowsky et al. | |
| 3,642,004 A | 2/1972 | Osthagen et al. | |
| 3,657,744 A | 4/1972 | Ersek | |
| 3,671,979 A | 6/1972 | Moulopoulos | |
| 3,714,671 A | 2/1973 | Edwards et al. | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,056,854 A | 11/1977 | Boretos et al. | |
| 4,106,129 A | 8/1978 | Carpentier et al. | |
| 4,233,690 A | 11/1980 | Akins | |
| 4,291,420 A | 9/1981 | Reul | |
| 4,425,908 A | 1/1984 | Simon | |
| 4,501,030 A | 2/1985 | Lane | |
| 4,531,943 A | 7/1985 | Van Tassel et al. | |
| 4,580,568 A | 4/1986 | Gianturco | |
| 4,602,911 A | 7/1986 | Ahmadi et al. | |
| 4,610,688 A | 9/1986 | Silvestrini et al. | |
| 4,617,932 A | 10/1986 | Kornberg | |
| 4,648,881 A | 3/1987 | Carpentier et al. | |
| 4,655,218 A | 4/1987 | Kulik et al. | |
| 4,655,771 A | 4/1987 | Wallsten | |
| 4,662,885 A | 5/1987 | DiPisa, Jr. | |
| 4,665,906 A | 5/1987 | Jervis | |
| 4,710,192 A | 12/1987 | Liotta et al. | |
| 4,733,665 A | 3/1988 | Palmaz | |
| 4,755,181 A | 7/1988 | Igoe | |
| 4,796,629 A | 1/1989 | Grayzel | |
| 4,819,751 A | 4/1989 | Shimada et al. | |
| 4,834,755 A | 5/1989 | Silvestrini et al. | |
| 4,856,516 A | 8/1989 | Hillstead | |
| 4,865,600 A | 9/1989 | Carpentier et al. | |
| 4,872,874 A | 10/1989 | Taheri | |
| 4,873,978 A | 10/1989 | Ginsburg | |
| 4,909,252 A | 3/1990 | Goldberger | |
| 4,917,102 A | 4/1990 | Miller et al. | |
| 4,927,426 A | 5/1990 | Dretler | |
| 4,986,830 A | 1/1991 | Owens et al. | |
| 4,994,077 A | 2/1991 | Dobben | |
| 5,002,556 A | 3/1991 | Ishida et al. | |
| 5,002,559 A | 3/1991 | Tower | |
| 5,064,435 A | 11/1991 | Porter | |
| 5,161,547 A | 11/1992 | Tower | |
| 5,163,953 A | 11/1992 | Vince | |
| 5,209,741 A | 5/1993 | Spaeth | |
| 5,258,023 A | 11/1993 | Reger | |
| 5,258,042 A | 11/1993 | Mehta | |
| 5,332,402 A | 7/1994 | Teitelbaum | |
| 5,336,258 A | 8/1994 | Quintero et al. | |
| 5,350,398 A | 9/1994 | Pavcnik et al. | |
| 5,370,685 A | 12/1994 | Stevens | |
| 5,389,106 A | 2/1995 | Tower | |
| 5,397,351 A | 3/1995 | Pavcnik et al. | |
| 5,411,552 A | 5/1995 | Andersen et al. | |
| 5,425,762 A | 6/1995 | Muller | |
| 5,431,676 A | 7/1995 | Dubrul et al. | |
| 5,443,495 A | 8/1995 | Buscemi et al. | |
| 5,443,499 A | 8/1995 | Schmitt | |
| 5,476,506 A | 12/1995 | Lunn | |
| 5,476,510 A | 12/1995 | Eberhardt et al. | |
| 5,480,423 A | 1/1996 | Ravenscroft et al. | |
| 5,507,767 A | 4/1996 | Maeda et al. | |
| 5,534,007 A | 7/1996 | St. Germain et al. | |
| 5,545,133 A | 8/1996 | Burns et al. | |
| 5,545,211 A | 8/1996 | An et al. | |
| 5,549,665 A | 8/1996 | Vesely et al. | |
| 5,554,183 A | 9/1996 | Nazari | |
| 5,554,185 A | 9/1996 | Block et al. | |
| 5,571,215 A | 11/1996 | Sterman et al. | |
| 5,573,520 A | 11/1996 | Schwartz et al. | |
| 5,575,818 A | 11/1996 | Pinchuk | |
| 5,645,559 A | 7/1997 | Hachtman et al. | |
| 5,662,671 A | 9/1997 | Barbut et al. | |
| 5,667,523 A | 9/1997 | Bynon et al. | |
| 5,674,277 A | 10/1997 | Freitag | |
| 5,693,083 A | 12/1997 | Baker et al. | |
| 5,695,498 A | 12/1997 | Tower | |
| 5,713,953 A | 2/1998 | Vallana et al. | |
| 5,716,370 A | 2/1998 | Williamson et al. | |
| 5,720,391 A | 2/1998 | Dohm et al. | |
| 5,725,552 A | 3/1998 | Kotula et al. | |
| 5,733,325 A | 3/1998 | Robinson et al. | |
| 5,735,842 A | 4/1998 | Krueger et al. | |
| 5,769,812 A | 6/1998 | Stevens et al. | |
| 5,807,405 A | 9/1998 | Vanney et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,055 A | 10/1998 | Spiridigliozzi et al. | |
| 5,824,056 A | 10/1998 | Rosenberg | |
| 5,824,064 A | 10/1998 | Taheri | |
| 5,843,158 A | 12/1998 | Lenker et al. | |
| 5,855,597 A | 1/1999 | Jayaraman | |
| 5,855,601 A | 1/1999 | Bessler et al. | |
| 5,860,966 A | 1/1999 | Tower | |
| 5,861,024 A | 1/1999 | Rashidi | |
| 5,861,028 A | 1/1999 | Angell | |
| 5,868,783 A | 2/1999 | Tower | |
| 5,876,448 A | 3/1999 | Thompson et al. | |
| 5,885,228 A | 3/1999 | Rosenman et al. | |
| 5,888,201 A | 3/1999 | Stinson et al. | |
| 5,891,191 A | 4/1999 | Stinson | |
| 5,895,399 A | 4/1999 | Barbut et al. | |
| 5,907,893 A | 6/1999 | Zadno-Azizi et al. | |
| 5,911,734 A | 6/1999 | Tsugita et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,070 A | 10/1999 | Bley et al. | |
| 5,984,957 A | 11/1999 | Laptewicz et al. | |
| 5,984,959 A | 11/1999 | Robertson et al. | |
| 5,984,973 A | 11/1999 | Girard et al. | |
| 5,993,469 A | 11/1999 | McKenzie et al. | |
| 5,997,557 A | 12/1999 | Barbut et al. | |
| 6,010,522 A | 1/2000 | Barbut et al. | |
| 6,022,370 A | 2/2000 | Tower | |
| 6,027,525 A | 2/2000 | Suh et al. | |
| 6,042,598 A | 3/2000 | Tsugita et al. | |
| 6,042,607 A | 3/2000 | Williamson et al. | |
| 6,093,203 A | 7/2000 | Uflacker | |
| 6,113,612 A | 9/2000 | Swanson et al. | |
| 6,123,723 A | 9/2000 | Konya et al. | |
| 6,142,987 A | 11/2000 | Tsugita | |
| 6,162,245 A | 12/2000 | Jayaraman | |
| 6,165,209 A | 12/2000 | Patterson et al. | |
| 6,168,579 B1 | 1/2001 | Tsugita | |
| 6,171,327 B1 | 1/2001 | Daniel et al. | |
| 6,174,322 B1 | 1/2001 | Schneidt | |
| 6,179,859 B1 | 1/2001 | Bates et al. | |
| 6,187,016 B1 | 2/2001 | Hedges et al. | |
| 6,197,053 B1 | 3/2001 | Cosgrove et al. | |
| 6,200,336 B1 | 3/2001 | Pavcnik et al. | |
| 6,206,909 B1 | 3/2001 | Hanada et al. | |
| 6,214,036 B1 | 4/2001 | Letendre et al. | |
| 6,221,006 B1 | 4/2001 | Dubrul et al. | |
| 6,221,096 B1 | 4/2001 | Aiba et al. | |
| 6,231,544 B1 | 5/2001 | Tsugita et al. | |
| 6,231,551 B1 | 5/2001 | Barbut | |

(56) References Cited

U.S. PATENT DOCUMENTS

| | | |
|---|---|---|
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |
| 6,312,465 B1 | 11/2001 | Griffin et al. |
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg et al. |
| 6,712,842 B1 | 3/2004 | Gifford et al. |
| 6,712,843 B2 | 3/2004 | Elliott |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor et al. |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh et al. |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne et al. |
| 7,413,563 B2 | 8/2008 | Corcoran et al. |
| 7,445,631 B2 | 11/2008 | Salahieh et al. |
| 7,455,689 B2 | 11/2008 | Johnson |
| 7,566,336 B2 | 7/2009 | Corcoran et al. |
| 7,582,104 B2 | 9/2009 | Corcoran et al. |
| 7,591,848 B2 | 9/2009 | Allen |
| 7,625,364 B2 | 12/2009 | Corcoran |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | LaFontaine |
| 7,748,389 B2 | 7/2010 | Salahieh et al. |
| 7,749,238 B2 | 7/2010 | Corcoran et al. |
| 7,780,725 B2 | 8/2010 | Haug et al. |
| 7,803,184 B2 | 9/2010 | McGuckin et al. |
| 7,803,186 B1 | 9/2010 | Li et al. |

(56) References Cited

U.S. PATENT DOCUMENTS

| | | |
|---|---|---|
| 7,824,442 B2 | 11/2010 | Salahieh et al. |
| 7,824,443 B2 | 11/2010 | Salahieh et al. |
| 7,896,915 B2 | 3/2011 | Guyenot et al. |
| 7,905,901 B2 | 3/2011 | Corcoran et al. |
| 7,927,351 B2 | 4/2011 | Corcoran et al. |
| 7,972,361 B2 | 7/2011 | Corcoran et al. |
| 8,043,368 B2 | 10/2011 | Crabtree |
| 8,057,540 B2 | 11/2011 | Letac et al. |
| 8,092,520 B2 | 1/2012 | Quadri |
| 8,167,935 B2 | 5/2012 | McGuckin et al. |
| 8,236,049 B2 | 8/2012 | Rowe et al. |
| 8,317,858 B2 | 11/2012 | Straubinger et al. |
| 8,366,741 B2 | 2/2013 | Chin et al. |
| 8,398,708 B2 | 3/2013 | Meiri et al. |
| 8,425,593 B2 | 4/2013 | Braido et al. |
| 8,444,689 B2 | 5/2013 | Zhang |
| 8,449,599 B2 | 5/2013 | Chau et al. |
| 8,551,132 B2 | 10/2013 | Eskridge et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,966 B2 | 11/2013 | Seguin et al. |
| 8,623,074 B2 | 1/2014 | Ryan |
| 8,628,566 B2 | 1/2014 | Eberhardt et al. |
| 8,673,000 B2 | 3/2014 | Tabor et al. |
| 8,685,080 B2 | 4/2014 | White |
| 8,721,708 B2 | 5/2014 | Sèguin et al. |
| 8,728,155 B2 | 5/2014 | Montorfano et al. |
| 8,740,962 B2 | 6/2014 | Finch et al. |
| 8,795,356 B2 | 8/2014 | Quadri et al. |
| 8,801,779 B2 | 8/2014 | Seguin et al. |
| 8,845,722 B2 | 9/2014 | Gabbay |
| 8,852,272 B2 | 10/2014 | Gross et al. |
| 8,870,948 B1 | 10/2014 | Erzberger et al. |
| 8,894,702 B2 | 11/2014 | Quadri et al. |
| 8,911,455 B2 | 12/2014 | Quadri et al. |
| 8,956,404 B2 | 2/2015 | Börtlein et al. |
| 8,986,375 B2 | 3/2015 | Garde et al. |
| 8,998,976 B2 | 4/2015 | Gregg et al. |
| 9,011,527 B2 | 4/2015 | Li et al. |
| 9,017,399 B2 | 4/2015 | Gross et al. |
| 9,023,074 B2 | 5/2015 | Theobald et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,060,857 B2 | 6/2015 | Nguyen et al. |
| 9,101,467 B2 | 8/2015 | Eberhardt et al. |
| 9,125,740 B2 | 9/2015 | Morriss et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,387,071 B2 | 7/2016 | Tuval et al. |
| 9,393,110 B2 | 7/2016 | Levi et al. |
| 9,393,112 B2 | 7/2016 | Tuval et al. |
| 9,414,913 B2 | 8/2016 | Beith et al. |
| 9,421,083 B2 | 8/2016 | Eidenschink et al. |
| 9,439,757 B2 | 9/2016 | Granada et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,563 B2 | 11/2016 | Li |
| 9,486,306 B2 | 11/2016 | Tegels et al. |
| 9,492,273 B2 | 11/2016 | Granada et al. |
| 9,498,330 B2 | 11/2016 | Solem |
| 9,504,564 B2 | 11/2016 | Nguyen et al. |
| 9,504,568 B2 | 11/2016 | Ryan |
| 9,510,943 B2 | 12/2016 | Mesana et al. |
| 9,554,899 B2 | 1/2017 | Granada et al. |
| 9,561,103 B2 | 2/2017 | Granada et al. |
| 9,579,198 B2 | 2/2017 | Deem et al. |
| 9,655,722 B2 | 5/2017 | Morriss et al. |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi et al. |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0187495 A1 | 10/2003 | Cully et al. |
| 2003/0199971 A1 | 10/2003 | Tower et al. |
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey et al. |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127936 A1 | 7/2004 | Salahieh et al. |
| 2004/0127979 A1 | 7/2004 | Wilson et al. |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |

(56) References Cited

U.S. PATENT DOCUMENTS

| | | |
|---|---|---|
| 2004/0220655 A1 | 11/2004 | Swanson et al. |
| 2004/0225321 A1 | 11/2004 | Krolik et al. |
| 2004/0225354 A1 | 11/2004 | Allen et al. |
| 2004/0254636 A1 | 12/2004 | Flagle et al. |
| 2005/0033402 A1 | 2/2005 | Cully et al. |
| 2005/0070934 A1 | 3/2005 | Tanaka et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0155312 A1 | 7/2006 | Levine et al. |
| 2006/0161249 A1 | 7/2006 | Realyvasquez et al. |
| 2006/0190030 A1 | 8/2006 | To et al. |
| 2006/0195183 A1 | 8/2006 | Navia et al. |
| 2006/0235510 A1 | 10/2006 | Johnson et al. |
| 2006/0247680 A1 | 11/2006 | Amplatz et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265045 A1 | 11/2006 | Shiu et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0203575 A1 | 8/2007 | Forster et al. |
| 2007/0244552 A1 | 10/2007 | Salahieh et al. |
| 2007/0255389 A1 | 11/2007 | Oberti et al. |
| 2007/0265656 A1 | 11/2007 | Amplatz et al. |
| 2007/0276324 A1 | 11/2007 | Laduca et al. |
| 2007/0288089 A1 | 12/2007 | Gurskis et al. |
| 2008/0015619 A1 | 1/2008 | Figulla et al. |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0140191 A1 | 6/2008 | Mathis et al. |
| 2008/0167682 A1 | 7/2008 | Corcoran et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0062841 A1 | 3/2009 | Amplatz et al. |
| 2009/0082803 A1 | 3/2009 | Adams et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1 | 2/2010 | Hill et al. |
| 2010/0049313 A1 | 2/2010 | Alan et al. |
| 2010/0094314 A1 | 4/2010 | Hernlund et al. |
| 2010/0121434 A1 | 5/2010 | Paul et al. |
| 2010/0161036 A1 | 6/2010 | Pintor et al. |
| 2010/0219092 A1 | 9/2010 | Salahieh et al. |
| 2010/0268204 A1 | 10/2010 | Tieu et al. |
| 2010/0280495 A1 | 11/2010 | Paul et al. |
| 2010/0284724 A1 | 11/2010 | Cardia |
| 2010/0298931 A1 | 11/2010 | Quadri et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0034987 A1 | 2/2011 | Kennedy |
| 2011/0218619 A1 | 9/2011 | Benichou et al. |
| 2011/0245911 A1 | 10/2011 | Quill et al. |
| 2011/0257723 A1 | 10/2011 | McNamara |
| 2011/0264198 A1 | 10/2011 | Murray et al. |
| 2011/0295363 A1 | 12/2011 | Girard et al. |
| 2011/0301702 A1 | 12/2011 | Rust et al. |
| 2012/0016464 A1 | 1/2012 | Seguin |
| 2012/0059458 A1 | 3/2012 | Buchbinder et al. |
| 2012/0078360 A1 | 3/2012 | Rafiee |
| 2012/0197283 A1 | 8/2012 | Marchand et al. |
| 2012/0197391 A1 | 8/2012 | Alkhatib et al. |
| 2013/0041447 A1 | 2/2013 | Erb et al. |
| 2013/0041458 A1 | 2/2013 | Lashinski et al. |
| 2013/0253643 A1 | 9/2013 | Rolando et al. |
| 2013/0261737 A1 | 10/2013 | Costello |
| 2013/0282110 A1 | 10/2013 | Schweich, Jr. et al. |
| 2013/0282114 A1 | 10/2013 | Schweich, Jr. et al. |
| 2013/0304197 A1 | 11/2013 | Buchbinder et al. |
| 2013/0310923 A1 | 11/2013 | Kheradvar et al. |
| 2013/0331931 A1 | 12/2013 | Gregg et al. |
| 2014/0005775 A1 | 1/2014 | Alkhatib et al. |
| 2014/0005778 A1 | 1/2014 | Buchbinder et al. |
| 2014/0012368 A1 | 1/2014 | Sugimoto et al. |
| 2014/0012374 A1 | 1/2014 | Rankin |
| 2014/0052237 A1 | 2/2014 | Lane et al. |
| 2014/0052244 A1 | 2/2014 | Rolando et al. |
| 2014/0067048 A1 | 3/2014 | Chau et al. |
| 2014/0214159 A1 | 7/2014 | Vidlund et al. |
| 2014/0222136 A1 | 8/2014 | Geist et al. |
| 2014/0243954 A1 | 8/2014 | Shannon |
| 2014/0249622 A1 | 9/2014 | Carmi et al. |
| 2014/0257476 A1 | 9/2014 | Montorfano et al. |
| 2014/0277390 A1 | 9/2014 | Ratz et al. |
| 2014/0324164 A1 | 10/2014 | Gross et al. |
| 2014/0330368 A1 | 11/2014 | Gloss et al. |
| 2014/0379076 A1* | 12/2014 | Vidlund ............ A61F 2/2418 623/2.18 |
| 2015/0039083 A1 | 2/2015 | Rafiee |

(56) References Cited

U.S. PATENT DOCUMENTS

| | | |
|---|---|---|
| 2015/0094802 A1 | 4/2015 | Buchbinder et al. |
| 2015/0112430 A1 | 4/2015 | Creaven et al. |
| 2015/0135506 A1 | 5/2015 | White |
| 2015/0142100 A1 | 5/2015 | Morriss et al. |
| 2015/0157457 A1 | 6/2015 | Hacohen |
| 2015/0173897 A1 | 6/2015 | Raanani et al. |
| 2015/0351903 A1 | 12/2015 | Morriss et al. |
| 2015/0351904 A1 | 12/2015 | Cooper et al. |
| 2016/0038280 A1 | 2/2016 | Morriss et al. |
| 2016/0151153 A1 | 6/2016 | Sandstrom et al. |
| 2016/0158000 A1 | 6/2016 | Granada et al. |
| 2016/0158003 A1 | 6/2016 | Wallace et al. |
| 2016/0166384 A1 | 6/2016 | Olson et al. |
| 2016/0310269 A1 | 10/2016 | Braido et al. |
| 2017/0035569 A1 | 2/2017 | Deem et al. |
| 2017/0042675 A1 | 2/2017 | Freudenthal |
| 2017/0209261 A1 | 7/2017 | Bortlein et al. |
| 2017/0209269 A1 | 7/2017 | Conklin |
| 2017/0231762 A1 | 8/2017 | Quadri et al. |
| 2017/0245991 A1 | 8/2017 | Granada et al. |
| 2018/0000580 A1 | 1/2018 | Wallace et al. |

FOREIGN PATENT DOCUMENTS

| | | |
|---|---|---|
| EP | 0409929 B1 | 4/1997 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1469797 B1 | 11/2005 |
| EP | 1600121 A1 | 11/2005 |
| EP | 1616531 A2 | 1/2006 |
| EP | 1849440 A1 | 10/2007 |
| EP | 2124826 B1 | 7/2014 |
| WO | WO95/04556 A2 | 2/1995 |
| WO | WO95/29640 A1 | 11/1995 |
| WO | WO96/14032 A1 | 5/1996 |
| WO | WO96/24306 A1 | 8/1996 |
| WO | WO98/36790 A1 | 8/1998 |
| WO | WO98/57599 A2 | 12/1998 |
| WO | WO99/44542 A2 | 9/1999 |
| WO | WO00/09059 A2 | 2/2000 |
| WO | WO00/44308 A2 | 8/2000 |
| WO | WO00/44313 A1 | 8/2000 |
| WO | WO00/67661 A2 | 11/2000 |
| WO | WO01/05331 A1 | 1/2001 |
| WO | WO01/35870 A1 | 5/2001 |
| WO | WO01/64137 A1 | 9/2001 |
| WO | WO02/36048 A1 | 5/2002 |
| WO | WO02/41789 A2 | 5/2002 |
| WO | WO02/100297 A2 | 12/2002 |
| WO | WO03/003943 A2 | 1/2003 |
| WO | WO03/003949 A2 | 1/2003 |
| WO | WO03/011195 A2 | 2/2003 |
| WO | WO03/030776 A2 | 4/2003 |
| WO | WO03/015851 A1 | 11/2003 |
| WO | WO03/094797 A1 | 11/2003 |
| WO | WO2004/014256 A2 | 2/2004 |
| WO | WO2004/019811 A2 | 3/2004 |
| WO | WO2004/026117 A2 | 4/2004 |
| WO | WO2004/041126 A1 | 5/2004 |
| WO | WO2004/047681 A1 | 6/2004 |
| WO | WO2004/066876 A1 | 8/2004 |
| WO | WO2004/082536 A1 | 9/2004 |
| WO | WO2005/037361 A2 | 4/2005 |
| WO | WO2005/084595 A1 | 9/2005 |
| WO | WO2005/087140 A1 | 9/2005 |
| WO | WO2009/072122 A1 | 6/2009 |
| WO | WO2009/108615 A1 | 9/2009 |
| WO | WO2009/132187 A1 | 10/2009 |
| WO | WO2009/137755 A2 | 11/2009 |
| WO | WO2010/141847 A1 | 12/2010 |
| WO | WO2013/158608 A1 | 10/2013 |
| WO | WO2013/158613 A1 | 10/2013 |
| WO | WO2016/168609 A1 | 10/2016 |

OTHER PUBLICATIONS

Atwood et al.; Insertion of Heart Valves by Catheterization; Project Supervised by Prof. S. Muftu of Northeastern University, May 2002: pp. 36-40.

Bodnar et al. Replacement Cardiac Valves; (Chapter 13) Extinct cardiac valve prostheses. Pergamon Publishing Corporation. New York, Aug. 1991: pp. 307-322.

Boudjemline et al. Percutaneous implantation of a biological valve in the aorta to treat aortic valve insufficiency —a sheep study.f Med Sci. Monit; Apr. 2002; vol. 8, No. 4: BR113-116.

Boudjemline et al. "Percutaneous implantation of a valve in the descending aorta in lambs." Euro. Heart J; Jul. 2002; 23: 1045-1049.

Boudjemline et al. "Percutaneous pulmonary valve replacement in a large right ventricular outflow tract: an experimental study." Journal of the Americal College of Cardiology; Mar. 2004; vol. 43(6): 1082-1087.

Boudjemline et al. "Percutaneous valve insertion: A new approach?" J. of Thoracic and Cardio. Surg; Mar. 2003; 125(3): 741-743.

Boudjemline et al. "Steps Toward Percutaneous Aortic Valve Replacement." Circulation; Feb. 2002; 105: 775-778.

Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43 (4): 698-703.

Cribier et al. "Percutaneous Transcatheter Implantation of an Aortic Valve Prosthesis for Calcific Aortic Stenosis: First Human Case Description." Circulation; Dec. 2002; 106: 3006-3008.

Cribier et al. "Percutaneous Transcatheter Implantation of an Aortic Valve Prosthesis for Calcific Aortic Stenosis: First Human Case." (slide presentation); TCT 2002 (conference); 16 pgs.; Washington D.C.; Sep. 24-28, 2002.

Ferrari et al. "Percutaneous transvascular aortic valve replacement with self expanding stent-valve device." Poster from the presentation given at SMIT 2000, 12th International Conference. 1 pg. Sep. 5, 2000.

Hijazi "Transcatheter Valve Replacement: A New Era of Percutaneous Cardiac Intervention Begins." J. of Am. College of Cardio; Mar. 2004; 43(6): 1088-1089.

Huber et al. "Do valved stents compromise coronary flow?" European Journal of Cardio-thoracic Surgery; May 2004; vol. 25: 754-759.

Knudsen et al. "Catheter-implanted prosthetic heart valves." Int'l J. of Art. Organs; May 1993; 16(5): 253-262.

Kort et al. "Minimally invasive aortic valve replacement: Echocardiographic and clinical results." Am. Heart J; Sep. 2001; 142(3): 476-481.

Love et al. fThe Autogenous Tissue Heart Valve: Current Stat.f Journal of Cardiac Surgery; Dec. 1991; 6(4): 499-507.

Lutter et al. "Percutaneous aortic valve replacement: An experimental study. I. Studies on implantation." J. of Thoracic and Cardio. Surg; Apr. 2002; 123(4): 768-776.

Moulopoulos et al. "Catheter-Mounted Aortic Valves." Annals of Thoracic Surg; May 1971; 11(5): 423-430.

Paniagua et al. "Percutaneous heart valve in the chronic in vitro testing model." Circulation; Sep. 2002; 106: e51-e52.

Paniagua et al. Heart Watch (2004). Texas Heart Institute. Spring (Mar. 2004) Edition: 8 pages.

Pavcnik et al. "Percutaneous bioprosthetic veno valve: A long-term study in sheep." J. of Vascular Surg; Mar. 2002; 35(3): 598-603.

Phillips et al. "A Temporary Catheter-Tip Aortic Valve: Hemodynamic Effects on Experimental Acute Aortic Insufficiency." Annals of Thoracic Surg; Feb. 1976; 21(2): 134-136.

(56) References Cited

OTHER PUBLICATIONS

Sochman et al. "Percutaneous Transcatheter Aortic Disc Valve Prosthesis Implantation: A Feasibility Study." Cardiovasc. Intervent. Radiol; Sep.-Oct. 2000; 23: 384-388.
Stuart, M. "In Heart Valves, A Brave, New Non-Surgical World." Start-Up; Feb. 2004: 9-17.
Vahanian et al. "Percutaneous Approaches to Valvular Disease." Circulation; Apr. 2004; 109: 1572-1579.
Van Herwerden et al., "Percutaneous valve implantation: back to the future?" Euro. Heart J; Sep. 2002; 23(18): 1415-1416.
Zhou et al. "Self-expandable valved stent of large size: off-bypass implantation in pulmonary position." Eur. J. Cardiothorac; Aug. 2003; 24: 212-216.
Wallace et al.; U.S. Appl. No. 15/669,788 entitled "Replacement cardiac valves and methods of use and manufacture," filed Aug. 4, 2017.
Granada et al.; U.S. Appl. No. 15/688,701 entitled "System and method for cardiac valve repair and replacement," filed Aug. 28, 2017.
Solvay; Novel revivent(tm) Myocardial anchoring system from bioVentrix uses solvay's zeniva® PEEK in tether component; 3 pages retrieved from the internet (http://www.solvay.com/en/media/press_release/20131205-novel-revivent-myocardial-anchoring-system-bioventrix-uses-zenivapeek.html); (Press Release); on Aug. 10, 2017.
Gregg et al.; U.S. Appl. No. 15/573,555 entitled "Cardiac valve delivery devices and systems," filed Nov. 13, 2017.

\* cited by examiner

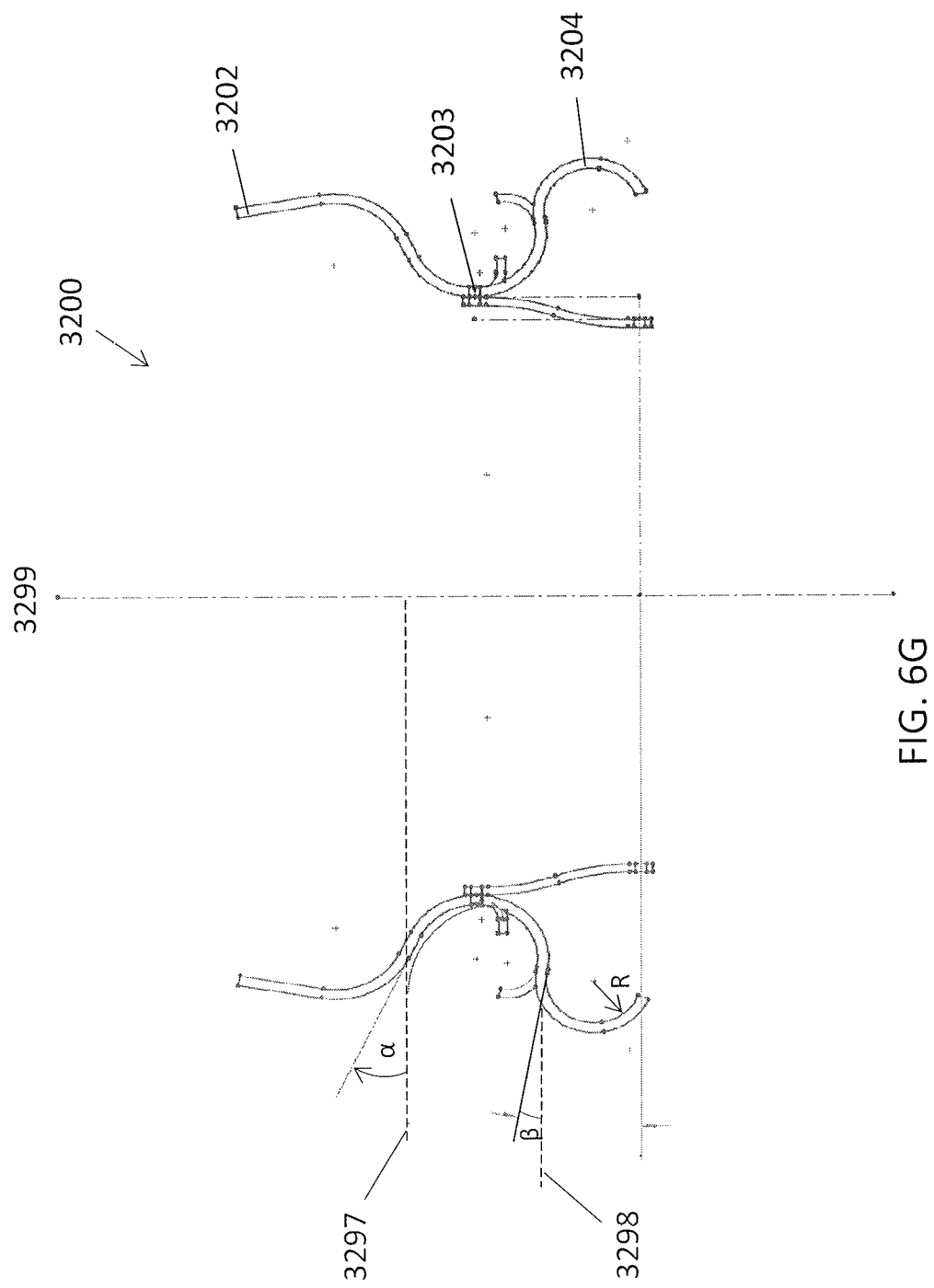

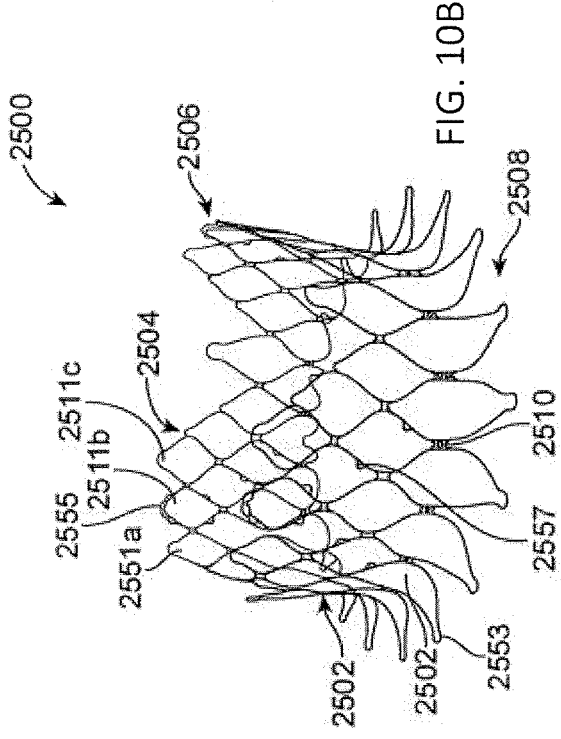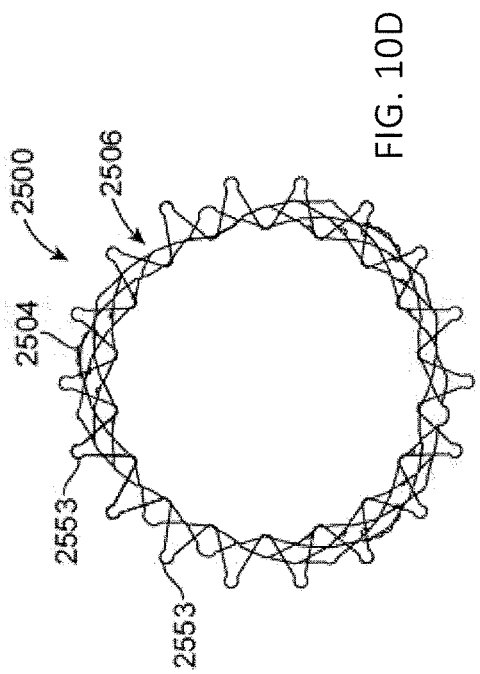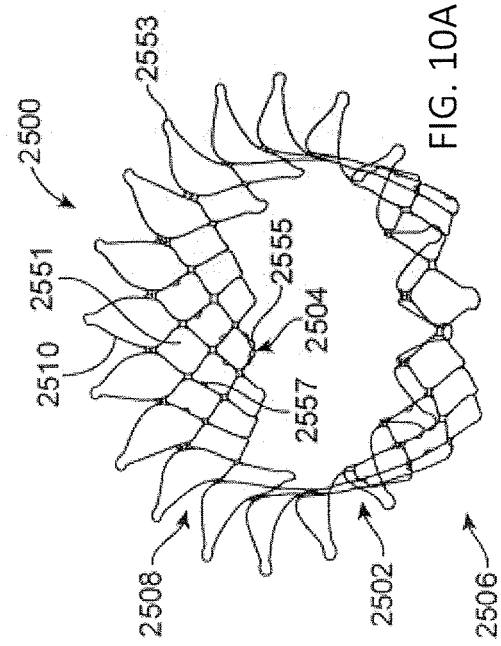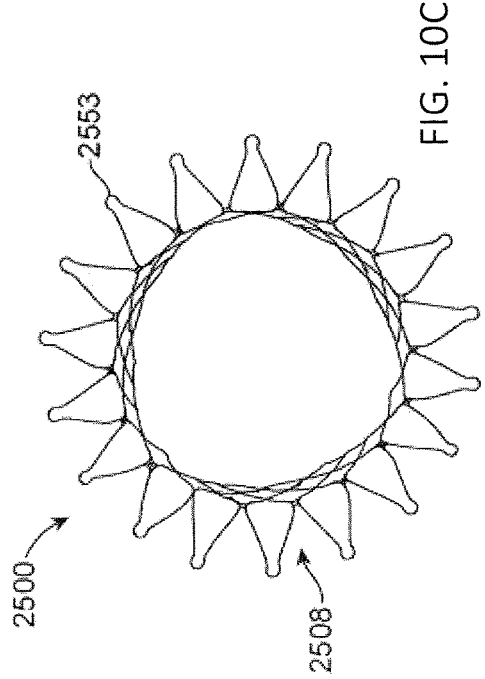

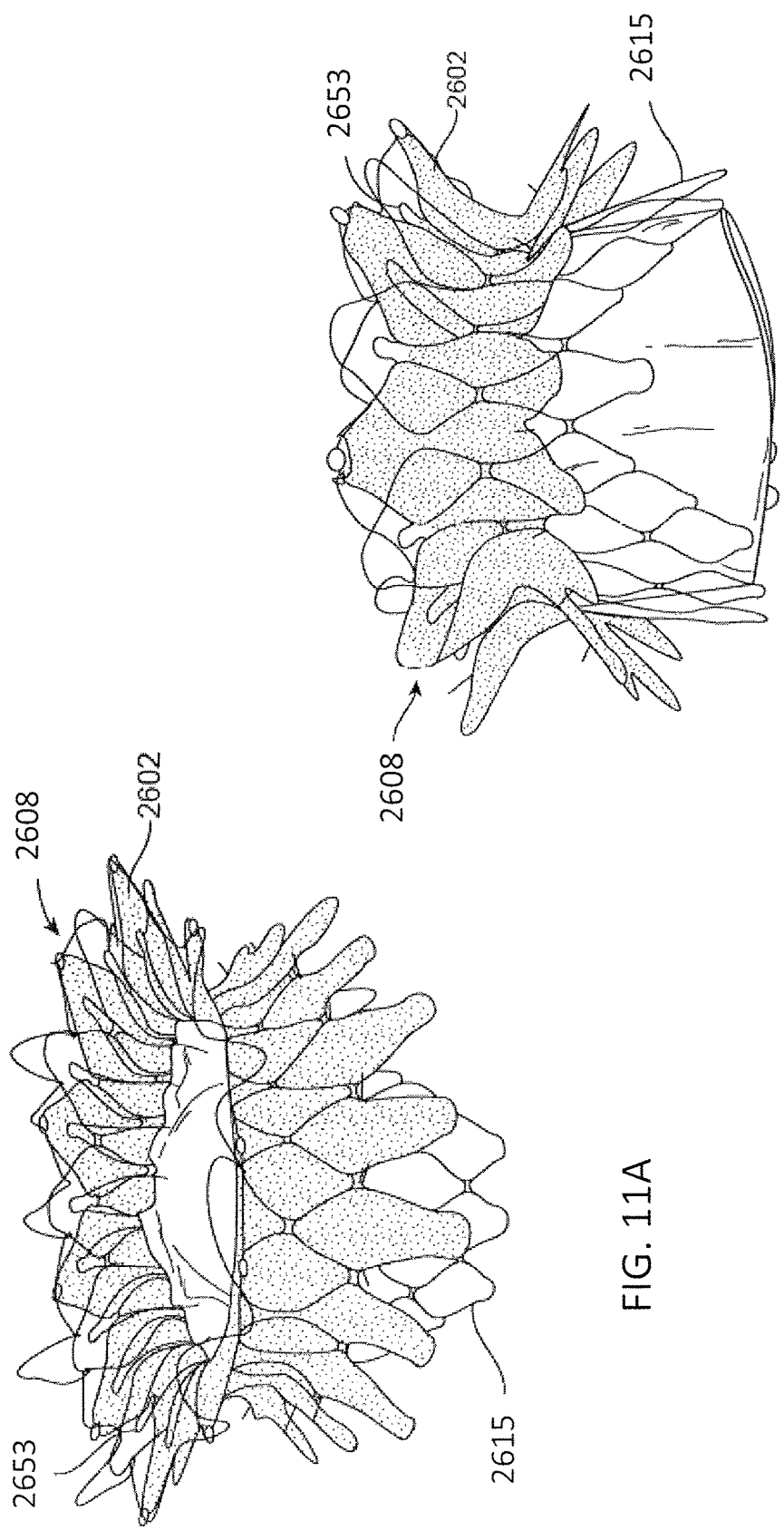

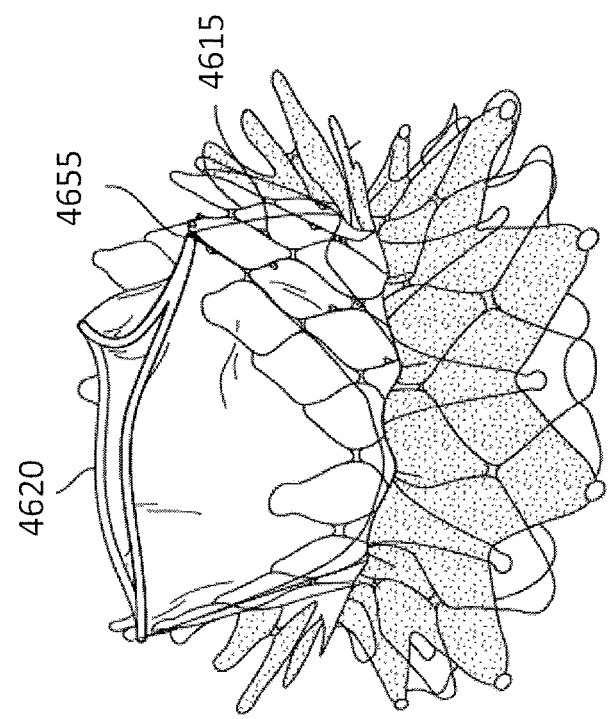
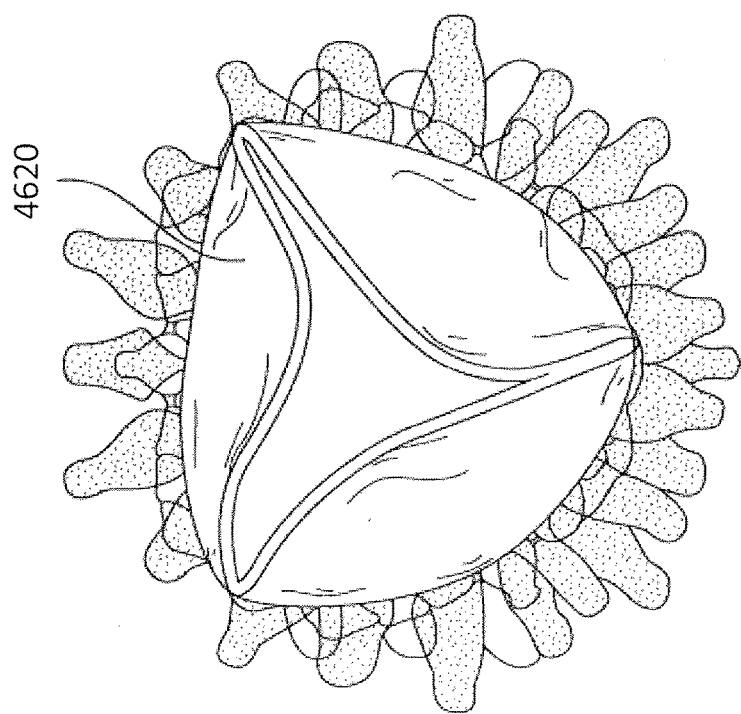
FIG. 13A
FIG. 13B

FIG. 15A
FIG. 15B
Fig. 15C
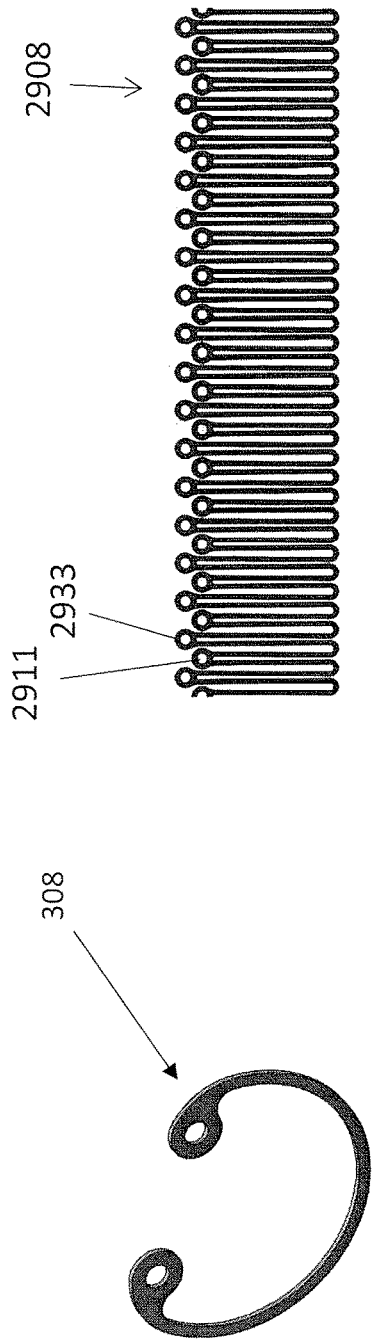
FIG. 15D

REPLACEMENT MITRAL VALVES

CROSS REFERENCE TO RELATED APPLICATIONS

This application is a continuation of International Patent Application No. PCT/US2016/032550, filed May 13, 2016, titled "REPLACEMENT MITRAL VALVES," now International Publication No. WO 2016/183526, which claims priority to U.S. Provisional Application No. 62/161,743, titled "REPLACEMENT MITRAL VALVES," and filed May 14, 2015, and to U.S. Provisional Patent Application No. 62/259,565, titled "REPLACEMENT MITRAL VALVES," and filed Nov. 24, 2015, the entireties of which is incorporated by reference herein.

This application may be related to U.S. patent application Ser. No. 14/170,388, filed Jan. 31, 2014, titled "SYSTEM AND METHOD FOR CARDIAC VALVE REPAIR AND REPLACEMENT," now U.S. Pat. No. 8,870,948, and U.S. patent application Ser. No. 14/677,320, filed Apr. 2, 2015, titled "REPLACEMENT CARDIAC VALVES AND METHODS OF USE AND MANUFACTURE," the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, such as problems with the mitral valve, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Minimally invasive aortic valve replacement devices, such as the Medtronic Corevalve or the Edwards Sapien, deliver aortic valve prostheses through small tubes which may be positioned within the heart through the aorta via the femoral artery or through the apex of the heart. However, the mitral valve differs from the aortic valve in that the shape and anatomy immediately surrounding the valve varies greatly from one side of the valve to the other. Moreover, current cardiac valve prostheses are not designed to function effectively within the mitral valve. Further, current cardiac valve prostheses delivered via a minimally invasive device are often difficult to place correctly within the native valve, difficult to match in size to the native valve, and difficult to retrieve and replace if initially placed incorrectly.

These and other deficiencies in existing approaches are described herein.

SUMMARY OF THE DISCLOSURE

In general, in one embodiment, a replacement mitral valve includes an anchor assembly including a ventricular anchor, an annular central portion, and an atrial anchor, an annular strut frame disposed radially within the anchor assembly, a central annular member between the anchor assembly and annular strut frame, and a plurality of replacement leaflets secured to the annular strut frame. The anchor assembly is configured to compress native cardiac tissue between the ventricular anchor and the atrial anchor. The central annular member is connected to both the anchor assembly and the annular strut frame so as to connect the anchor assembly to the annular strut frame.

This and other embodiments can include one or more of the following features. A ventricular end of the central annular member can have a smaller diameter than a diameter of the atrial end of the central annular member. The diameter of the ventricular end can be between 25 mm and 30 mm, and the diameter of the atrial end is between 30 mm and 35 mm. The central annular member can include a plurality of linear posts extending from an atrial end to a ventricular end and a plurality of zig-zag circumferential members extending circumferentially therearound. The central annular member can have a lower spring constant than the strut frame. The strut frame can have a higher spring constant than the anchor assembly. The central annular member can include a suspension. The central annular member and the anchor assembly can be connected together with couplers. The central annular member and the annular strut frame can be connected together with couplers. The central annular member can be configured to minimize deformation of replacement leaflet alignment in response to deformation of an expandable anchor. The device can be configured to self-expand from a constrained configuration to an expanded configuration. The device can be configured to foreshorten upon expansion of the atrial anchor, ventricular anchor, and central portion from the constrained configuration to the expanded configuration.

In general, in one embodiment, a replacement mitral valve includes an anchor assembly comprising a ventricular anchor, an annular central portion, and an atrial anchor, an annular strut frame disposed radially within the anchor assembly, a suspension connecting the anchor assembly to the annular strut frame, and a plurality of replacement leaflets secured to the annular strut frame. The anchor assembly is configured to compress native cardiac tissue between the ventricular anchor and the atrial anchor.

This and other embodiments can include one or more of the following features. The suspension can have a lower spring constant than the strut frame. The strut frame can have a higher spring constant than the anchor assembly. The suspension can include a plurality of springs. The springs can be leaf springs. The suspension and the anchor assembly can be connected together with couplers. The suspension and the annular strut frame can be connected together with couplers. The suspension can be configured to minimize deformation of replacement leaflet alignment in response to deformation of an expandable anchor. The device can be configured to self-expand from a constrained configuration to an expanded configuration. The device can be configured to foreshorten upon expansion of the atrial anchor, ventricular anchor, and central portion from the constrained configuration to the expanded configuration.

In general, in one embodiment, a prosthetic mitral valve includes an anchor assembly including an atrial anchor, a ventricular anchor, and a central portion therebetween, and a plurality of replacement leaflets coupled with the anchor assembly. The atrial anchor or the ventricular anchor includes an annular frame having plurality of pear-shaped extensions connected together. The anchor assembly is configured to self-expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor.

This and other embodiments can include one or more of the following features. The annular frame can be substantially circular. The device can be configured to foreshorten upon expansion of the atrial anchor, ventricular anchor, and central portion from the constrained configuration to the expanded configuration. The atrial anchor and the ventricular anchor can each have a diameter in the expanded configuration that is greater than a diameter of the central portion in the expanded configuration. The atrial anchor and the ventricular can include an annular frame having a plurality of pear-shaped extensions connected together. At least two of the plurality of pear-shaped extensions can have different lengths from one another. Each of the plurality of pear-shaped extensions can include an inner rounded portion and an outer rounded portion. The inner rounded portion can have a smaller diameter than a diameter of the outer rounded portion. The diameter of the inner rounded portion can be between 2 mm and 3 mm, and the diameter of the outer rounded portion can be between 5 mm and 6 mm. The atrial anchor, ventricular anchor, and central portion can all be integral with one another. The prosthetic mitral valve can further include an annular strut frame secured radially within the anchor assembly. The annular strut frame can be configured to support the plurality of replacement leaflets. When the anchor assembly is in the expanded configuration, extensions on the ventricular anchor can curve around to point at least partially radially inwards. When the anchor assembly is in the expanded configuration, extensions of the atrial anchor point can be substantially in the atrial direction.

In general, in one embodiment, a prosthetic mitral valve includes an anchor assembly including an atrial anchor, a ventricular anchor, and a central portion therebetween, and a plurality of replacement leaflets coupled with the anchor assembly. The atrial anchor or the ventricular anchor includes an annular frame having plurality of extensions connected together, wherein there are at least two extensions of differing radial lengths. The anchor assembly is configured to self-expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor.

This and other embodiments can include one or more of the following features. The annular frame can be substantially circular. The device can be configured to foreshorten upon expansion of the atrial anchor, ventricular anchor, and central portion from the constrained configuration to the expanded configuration. The atrial anchor and the ventricular anchor can each have a diameter in the expanded configuration that is greater than a diameter of the central portion in the expanded configuration. The atrial anchor or the ventricular anchor can include a plurality of pear-shaped extensions connected together. The atrial anchor, ventricular anchor, and central portion can all be integral with one another. The prosthetic mitral valve can further include an annular strut frame secured radially within the anchor assembly. The annular strut frame can be configured to support the plurality of replacement leaflets. When the anchor assembly is in the expanded configuration, extensions on the ventricular anchor can curve around to point at least partially radially inwards. When the anchor assembly is in the expanded configuration, extensions of the atrial anchor can point substantially in the atrial direction.

At least one extension can have a radial length that is between 1 mm and 3 mm longer than another extension. The plurality of extensions can include a plurality of first extensions having a first radial length and a plurality of second extensions having a second radial length. The first and second extensions can be arranged in an alternating pattern around the annular frame.

In general, in one embodiment, a prosthetic mitral valve includes an anchor assembly including an atrial anchor, a ventricular anchor, and a central portion therebetween, and a plurality of replacement leaflets coupled with the anchor assembly. The ventricular anchor includes an annular frame having plurality of extensions connected together. The anchor assembly is configured to self-expand from a constrained configuration to an expanded configuration in which the ventricular anchor and the atrial anchor are flared radially outward relative to the central portion and ends of the extensions on the ventricular anchor curve around to point at least partially radially inwards. The anchor assembly in the expanded configuration is configured to compress native cardiac tissue between the ventricular anchor and the atrial anchor.

This and other embodiments can include one or more of the following features. The annular frame can be substantially circular. The device can be configured to foreshorten upon expansion of the atrial anchor, ventricular anchor, and central portion from the constrained configuration to the expanded configuration. The atrial anchor and the ventricular anchor each have a diameter in the expanded configuration that is greater than a diameter of the central portion in the expanded configuration. The atrial anchor or the ventricular anchor includes a plurality of pear-shaped extensions connected together. The atrial anchor, ventricular anchor, and central portion can all be integral with one another. The prosthetic mitral valve can further include an annular strut frame secured radially within the anchor assembly. The annular strut frame can be configured to support the plurality of replacement leaflets. When the anchor assembly is in the expanded configuration, extensions of the atrial anchor can point substantially in the atrial direction. At least two of the plurality of pear-shaped extensions can have different lengths from one another. A radius of curvature formed by the curved ends of the extensions of the ventricular anchor can be between approximately 0.1" and 0.2."

In general in one embodiment, a prosthetic mitral valve includes an anchor assembly including an atrial anchor, a ventricular anchor, and a central portion therebetween, and a plurality of replacement leaflets coupled with the anchor assembly. The atrial anchor includes an annular frame having plurality of extensions connected together. The anchor assembly is configured to self-expand from a constrained configuration to an expanded configuration in which the ventricular anchor and the atrial anchor are flared radially outward relative to the central portion and ends of the extensions on the atrial anchor point substantially in the atrial direction. The anchor assembly in the expanded configuration is configured to compress native cardiac tissue between the ventricular anchor and the atrial anchor.

This and other embodiments can include one or more of the following features. The annular frame can be substantially circular. The device can be configured to foreshorten upon expansion of the atrial anchor, ventricular anchor, and central portion from the constrained configuration to the expanded configuration. The atrial anchor and the ventricular anchor can each have a diameter in the expanded configuration that is greater than a diameter of the central portion in the expanded configuration. The atrial anchor or the ventricular anchor can include a plurality of pear-shaped extensions connected together. The atrial anchor, ventricular anchor, and central portion can all be integral with one another. The prosthetic mitral valve can further include an annular strut frame secured radially within the anchor assembly. The annular strut frame can be configured to support the plurality of replacement leaflets. When the anchor assembly is in the expanded configuration, extensions on the ventricular anchor can curve around to point at least partially radially inwards. At least two of the plurality of pear-shaped extensions can have different lengths from one another.

In general, in one embodiment, a replacement mitral valve includes an anchor assembly including a ventricular anchor, an annular central portion, and an atrial anchor, an annular strut frame disposed radially within the anchor assembly, and a plurality of replacement leaflets secured to the annular strut frame. The anchor assembly is configured to expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor. The annular strut frame is flared radially outward to form a funnel shape on an atrial side of the strut frame.

This and other embodiment can include one or more of the following features. The replacement mitral valve can further include a plurality of ovoid strut attachment mechanisms extending from the annular strut frame. The ovoid strut attachment mechanisms can be configured for sewing attachment of the replacement leaflets. The annular strut frame can be attached to the anchor assembly with a plurality of couplers. The plurality of couplers can be rivets. The annular strut frame can be attached to the anchor assembly through a central annular member. The annular strut frame can be attached to the anchor assembly through a suspension. The atrial anchor can further include a flared atrial portion, wherein the flared atrial portion of the atrial anchor and the flare of the annular strut frame can be configured to substantially conform to one another. The strut frame can flare at an angle of approximately 60-65 degrees relative to a central axis of the mitral valve.

In general, in one embodiment, a replacement mitral valve includes an anchor assembly including a ventricular anchor, an annular central portion, and an atrial anchor, an annular strut frame disposed radially within the anchor assembly, and a plurality of replacement leaflets secured to the annular strut frame. The anchor assembly is configured to expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor. The annular strut frame has a plurality of rivet holes at a ventricular end of the strut frame configured for attachment to the anchor assembly.

This and other embodiments can include one or more of the following features. The replacement mitral valve can further include a plurality of ovoid strut attachment mechanisms extending from the annular strut frame. The ovoid strut attachment mechanisms can be configured for sewing attachment of the replacement leaflets. The annular strut frame can be attached to the anchor assembly with a plurality of couplers. Each coupler can extend through a hole of the plurality of holes. The plurality of couplers can be rivets. The anchor assembly can further include a plurality of holes. A coupler can extend through each of the holes of the anchor assembly for attachment to the annular strut frame. The annular strut frame can be attached to the anchor assembly through a central annular member. The annular strut frame can be attached to the anchor assembly through a suspension.

In general, in one embodiment, a replacement mitral valve includes an anchor assembly comprising a ventricular anchor, an annular central portion, and an atrial anchor, an annular strut frame disposed radially within the anchor assembly, and a plurality of replacement leaflets secured to the annular strut frame. The anchor assembly is configured to expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor. The annular strut frame includes a suture extending around an entire circumference of the annular strut frame to prevent flaring of one end of the annular strut frame relative to another during delivery of the replacement valve.

In general, in one embodiment, a prosthetic mitral valve includes an anchor assembly including an atrial anchor, a ventricular anchor, and a central portion therebetween, and a plurality of replacement leaflets coupled with the anchor assembly. The atrial anchor or the ventricular anchor includes an annular frame having plurality of peaks and valleys extending around the circumference. A hook is positioned in one or more of the valleys configured to engage tissue. The anchor assembly is configured to self-expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor.

In general, in one embodiment, a prosthetic mitral valve includes an anchor assembly including an atrial anchor, a ventricular anchor, and a central portion therebetween, and a plurality of replacement leaflets coupled with the anchor assembly. A plurality of hooks extend from the central portion configured to engage tissue. The anchor assembly is configured to self-expand from a constrained configuration to an expanded configuration in which the ventricular anchor and the atrial anchor are flared radially outward relative to the central portion. The anchor assembly in the expanded configuration is configured to compress native cardiac tissue between the ventricular anchor and the atrial anchor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 6G is a cross-section of the valve prosthesis of FIG. 6A without the skirt or leaflets attached thereto.

FIGS. 10A-10D show various view of a strut frame.

FIGS. 11A-11B shows another embodiment of a valve prosthesis.

FIGS. 13A-13B show another embodiment of a valve prosthesis.

FIGS. 15A-15D show various embodiments of spring members.

DETAILED DESCRIPTION

Figure 1:
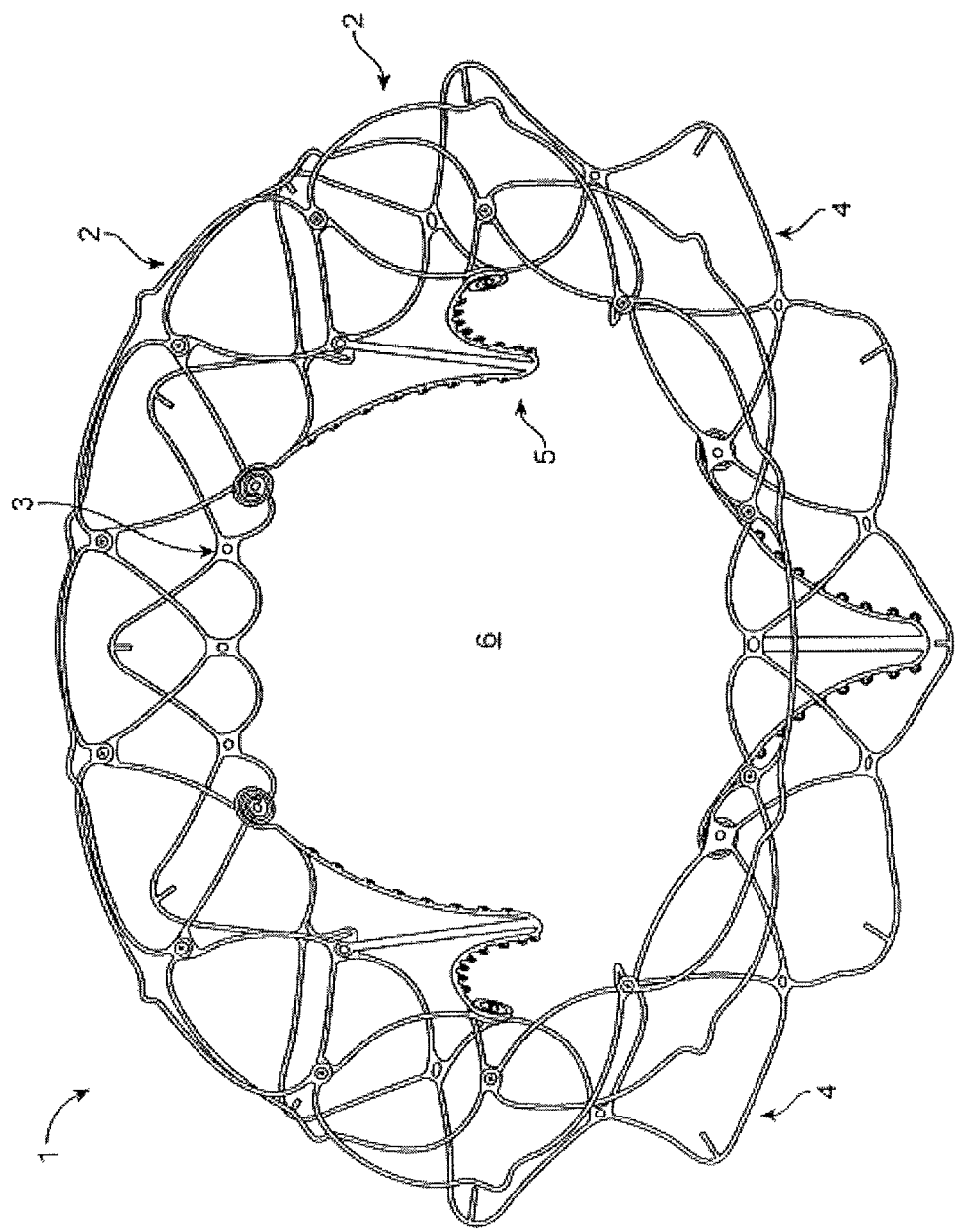
FIG. 1 shows a portion of an embodiment of a valve prosthesis in an expanded configuration.

This disclosure includes replacement heart valves (also referred herein as prosthetic heart valves), methods of manufacturing replacement heart valves, including subassemblies thereof, and methods of using replacement heart valves. This disclosure describes the prostheses in the context of replacement mitral valves, but it is conceivable that the prostheses herein can be used or modified to be used as other replacement heart valves. In some embodiments, the replacement heart valves are self-orienting (at least on one side) replacement mitral valves configured to be delivered using minimally invasive techniques.

The replacement heart valves herein include an expandable anchor that includes an atrial anchor (e.g., configured to be placed on an atrial side of a mitral valve annulus), a ventricular anchor (e.g., configured to be placed on a ventricular side of a mitral valve annulus), and a central portion axially between the atrial and ventricular anchors. The expandable anchor is adapted to be collapsed towards a collapsed delivery configuration, and is adapted to expand towards an expandable configuration. The replacement heart valves also include a plurality of struts or strut frame secured to at least one of the central portion, the ventricular anchor, or the atrial anchor for securing a plurality of replacement leaflets thereto. The struts or strut frame can be considered part of the expandable anchor, and in embodiments herein are configured to deform as the rest of the expandable anchor is collapsed. It may be possible to incorporate struts that are not deformable, but which are still secured to the expandable anchor. These types of struts may not be considered part of the expandable anchor but are secured to the expandable anchor. The struts extend distally, that is, towards the ventricular anchor. In the context of replacement mitral valves, the "distal" end of the replacement valve refers to the end of the replacement valve that is to be positioned on the ventricular side of the annulus, while "proximal" end refers to the end of the replacement valve that is to be positioned on the atrial side of the annulus. "Distally" in the context of trans-atrial delivery can be used to refer to a location closer to the left ventricle than the left atrium, while "proximally" is generally used to refer to a location closer to the left atrium than the left ventricle.

In some embodiments, the expandable anchor is adapted to completely self-expand, and in some embodiments it is configured to be partially self-expanding and partially expand by non-self-expanding influences (e.g., a balloon). The expandable anchors can be made of (or partly made of) a super elastic material such as nitinol.

In methods of use, the prostheses described herein can be delivered to a cardiac valve orifice, such as the mitral valve, by using minimally invasive techniques to access the cardiac valve. Access routes and procedures are known, such as making small incisions in the patient's body and passing the prosthesis through the apex of the heart to, for example, a mitral valve. An additional exemplary access route includes delivering the valve through the venous system and into the left atrium via a transseptal puncture. A transseptal approach can impart size limitations on the delivery and thus the delivery profile of the replacement heart valve. Additionally, a transseptal approach can also impart certain flexibility requirements on the replacement heart valve. The replacement heart valves herein are configured to be collapsed into a delivery configuration so they can fit within a delivery device. The replacement heart valves can be delivered to the treatment site within the delivery device and then deployed from the delivery device. If necessary, the replacement valves can be repositioned, re-sheathed (partially or completely) if necessary, and then re-deployed.

Replacement heart valves herein are configured to be secured in the native valve orifice by sandwiching the cardiac orifice between ventricular and atrial anchors, which are larger in diameter than the valve orifice, and by applying a radial force from the center portion outward against the cardiac orifice. Additional engagement between the prostheses and cardiac tissue can be added with wire hooks extending from the valve prostheses.

Figure 2:
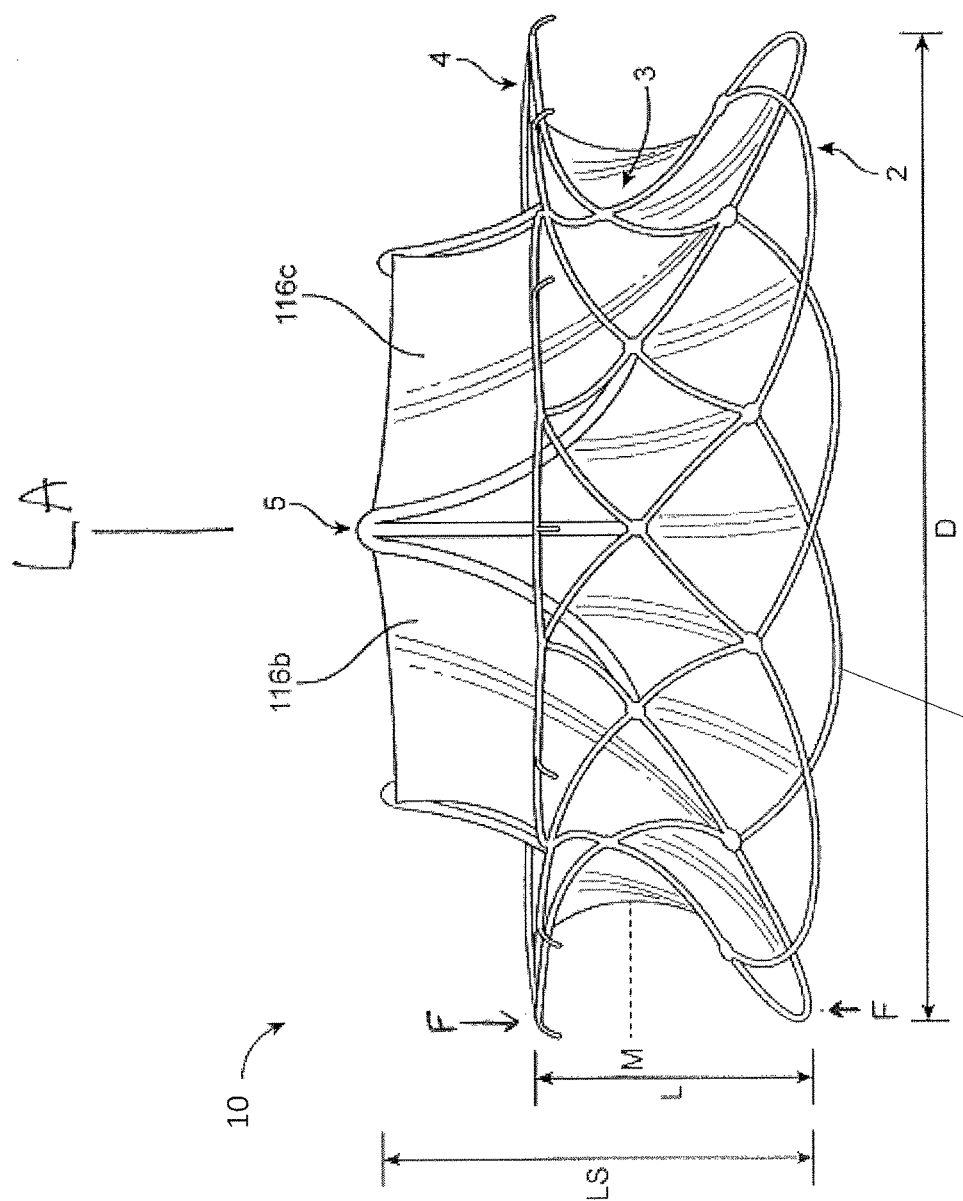
FIG. 2 is a side view illustrating the prosthesis of FIG. 1 including leaflets.
Figure 3:
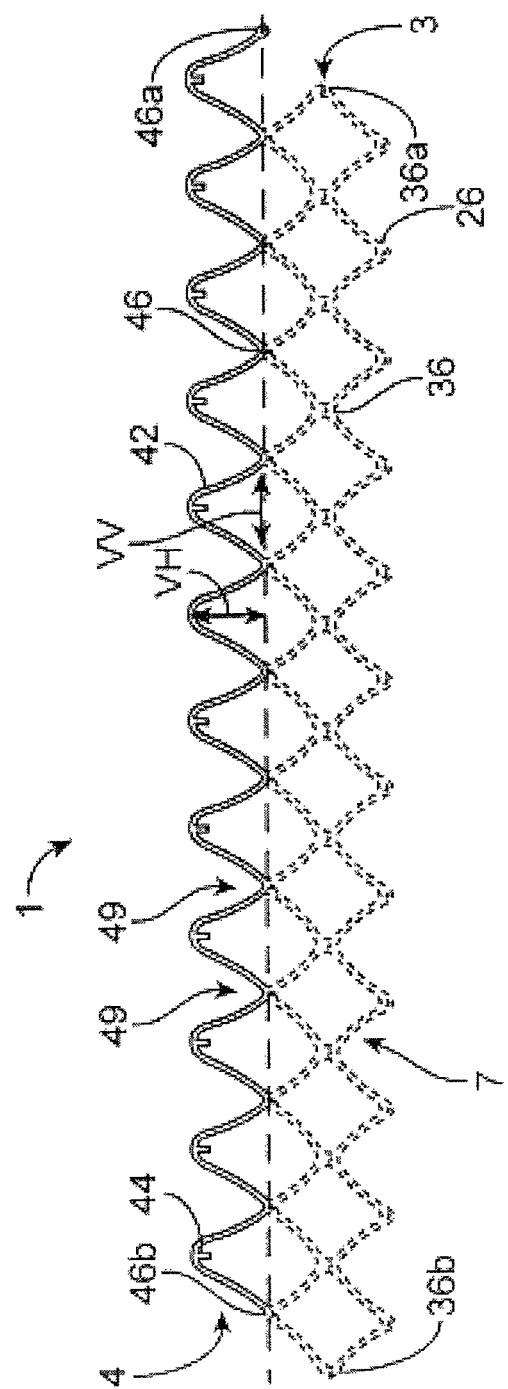
FIG. 3 illustrates an integral central portion and ventricular anchor after being cut from a sheet of material.

FIGS. 1-3 show an exemplary mitral valve prosthesis 10 in an expanded configuration after an expandable anchor and struts have been secured together. The portion of the replacement valve shown in FIG. 1 may be referred to as an anchor subassembly, which includes an expandable anchor 1 and struts 5, but excludes leaflets and any skirts that may be incorporated into the final replacement valve. Expandable anchor 1 includes an atrial anchor 2, a ventricular anchor 4, and a central portion 3 therebetween. In this embodiment, atrial anchor 2 is configured and adapted to be disposed on an atrial side of a mitral valve orifice, and ventricular anchor 4 is configured and adapted to be disposed on a ventricle side of the mitral valve orifice. In some uses, however, expandable anchor 1 may be implanted so that atrial anchor 2 as shown is positioned on the ventricle side and ventricular anchor 4 is positioned on the atrial side. The anchor subassembly and/or struts can be made of wire, such as a metal wire, such as nitinol.

Three struts 5 are secured to the anchor subassembly 1, and in this embodiment are secured to central portion 3, and at least a portion of struts 5 are disposed radially inward relative to central portion 3. Struts 5 are extending, or pointing, towards ventricular anchor 4 and away from atrial anchor 2.

Radially inner surfaces of the expandable anchor and the struts define central opening 6, which is radially within the expandable anchor. The radially inner surfaces of central portion 3 substantially define the perimeter of central opening 6. Replacement leaflets, which are not shown in FIG. 1 for clarity, are secured to struts 5 and are disposed at least partially in central opening 6, and are configured to control blood flow therethrough.

In this embodiment, atrial anchor 2 includes overlapping arches 32 extending around the perimeter of the anchor 2. Ventricular anchor 4 includes a plurality of arches 42 that extend from the central portion towards the ventricular end. A plurality of spaces 49 (see FIG. 3) extend between adjacent arches 42, the configurations and sizes of which are defined by the configuration of adjacent arches 42, are configured to advantageously allow the sub-valvular structures, such as chords, to slide between adjacent arches 42 when the ventricular anchor is expanded on the ventricular side of the mitral valve annulus. The arch 32, 42 tips are rounded, or curved (as opposed to abrupt or sharp) to avoid damaging the tissue when implanted.

In the expanded configuration shown in FIG. 1 (which is also an "as-manufactured" configuration), atrial anchor 2 and ventricular anchor 4 extend radially outward from central portion 3, and are considered to flare outward relative to central portion 4. Atrial anchor 2 and ventricular anchor 4 can also be considered flanged relative to central portion 3. The flared configuration of atrial and ventricular anchors 2 and 4 relative to central portion 3 is described in the context of a side view of the expandable anchor, as can be seen in FIG. 2 (which illustrates leaflets secured to struts).

In some embodiments, one or more of the flared anchors are orthogonal to a longitudinal axis "LA" (illustrated in FIG. 2) passing through central opening 6. In some embodiments, the flared anchor portions have a smooth curve radially outward. In some flared configuration the two anchors and the central portion define a general "C" or "U" shape in a side view of the expandable anchor. A "C" or "U" configuration is not limited to symmetrical configurations, however, as there can be slight deviation from a true "U" and still be considered to be U-shaped. For example, the expandable anchor could define a "C" configuration, but one of the atrial and ventricular anchors could have a tighter curvature than the other anchor. When the anchor portions are flared and create a "C" shaped configuration, the atrial and ventricular anchors are slightly curved inward towards the central portion at their respective ends. In some embodiments, atrial anchor 2 and ventricular anchor 4 are substantially parallel to one another, such as exactly parallel to one another. In some embodiments the configuration of the flared anchors creates a substantially constant radius of curvature (i.e., a semi-circle) so that stress across anchors 2 and 4, and central portion 4 is balanced, thereby reducing fatigue or wear at any one point along the prosthesis. In other embodiments, the flared configuration of the two anchors and the central portion define a general hour-glass shape in a side view of the expandable anchor (see, e.g., FIGS. 6F and 6G). That is, the anchor portions can be flared outwards relative to the central portion and then curved or bent to point at least partially back in the axial direction. Again, an hour glass configuration is not limited to symmetrical configuration.

Figure 10E:
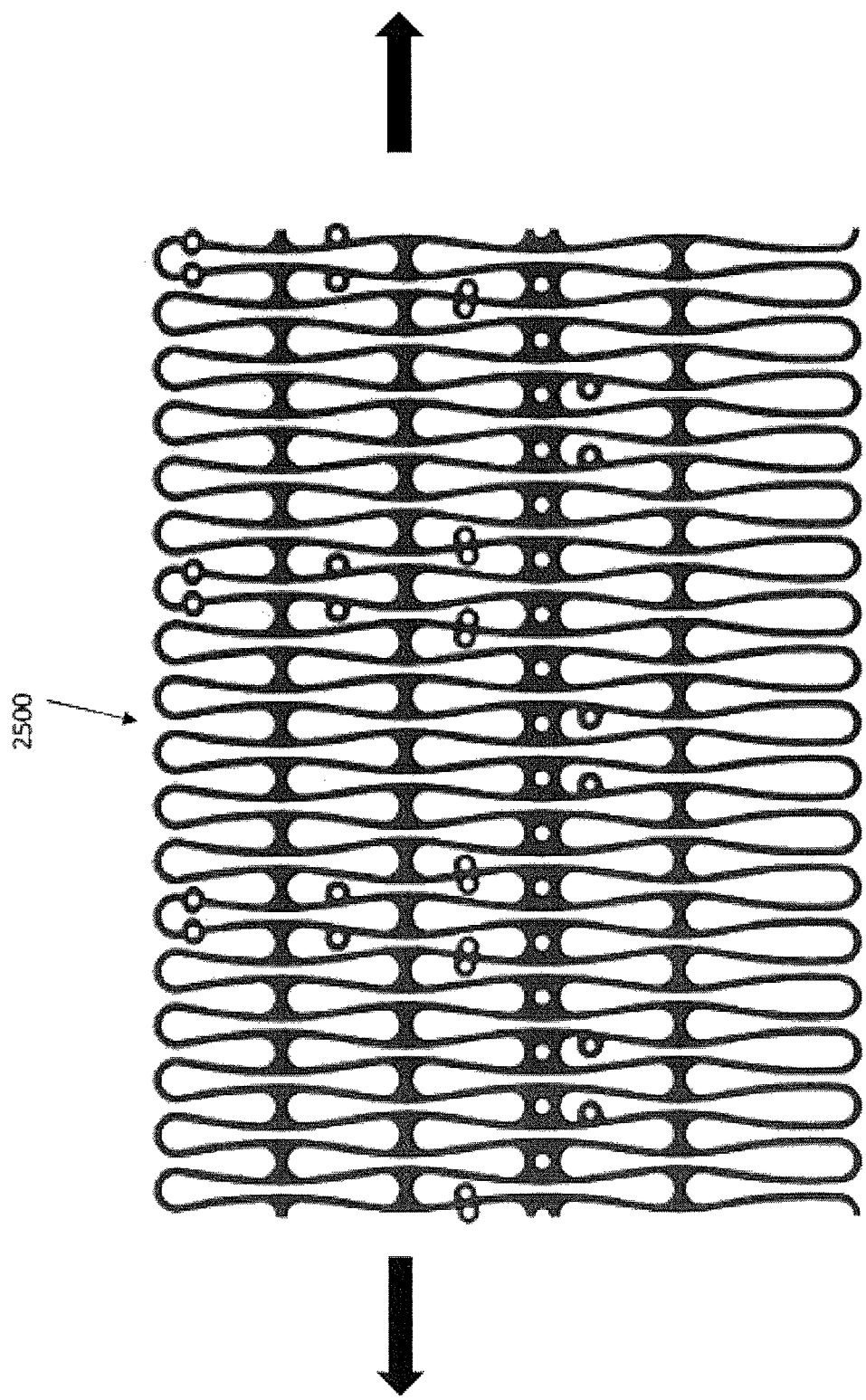
FIG. 10E shows the strut frame of FIGS. 10A-10D flattened.

In some embodiments the expanded anchor 1 (not including the struts) has a length "L" (see FIG. 2, measured from the atrial end to the ventricular end, parallel to the longitudinal axis LA) of 6-12 mm, such as 6-11 mm, 6-10 mm, 6-9 mm, 7-11 mm, 8-10 mm, 6 mm, 7 mm, 8 mm, 9 mm, 10 mm, 11 mm, and 12 mm. In some embodiments the length of the expanded prosthesis, including the struts ("LS" as shown in FIG. 2), has a length of 16-20 mm, such as 17-19 mm, 16 mm, 17 mm, 18 mm, 19 mm, and 20 mm with the struts. In some embodiments, the expanded anchor has an expanded diameter ("D" in FIG. 2) of about 35 mm to about 75 mm, such as about 45 mm to about 65 mm. In some of those embodiments the device is configured to be collapsed to a collapsed configuration in which it has a collapsed diameter D of 7 mm to 12 mm (i.e., the prosthesis can be collapsed down to fit within a 21-36 French catheter). In some embodiments the central opening 6 diameter is between 20 mm and 45 mm, such as between 25 mm and 40 mm, such as between 28 mm and 38 mm. In embodiments in which central opening 6 is not a perfect circle, the central opening diameter refers to the greatest linear dimension between points on the central portion, when viewed in an end view such as FIG. 10A.

Figure 4A:
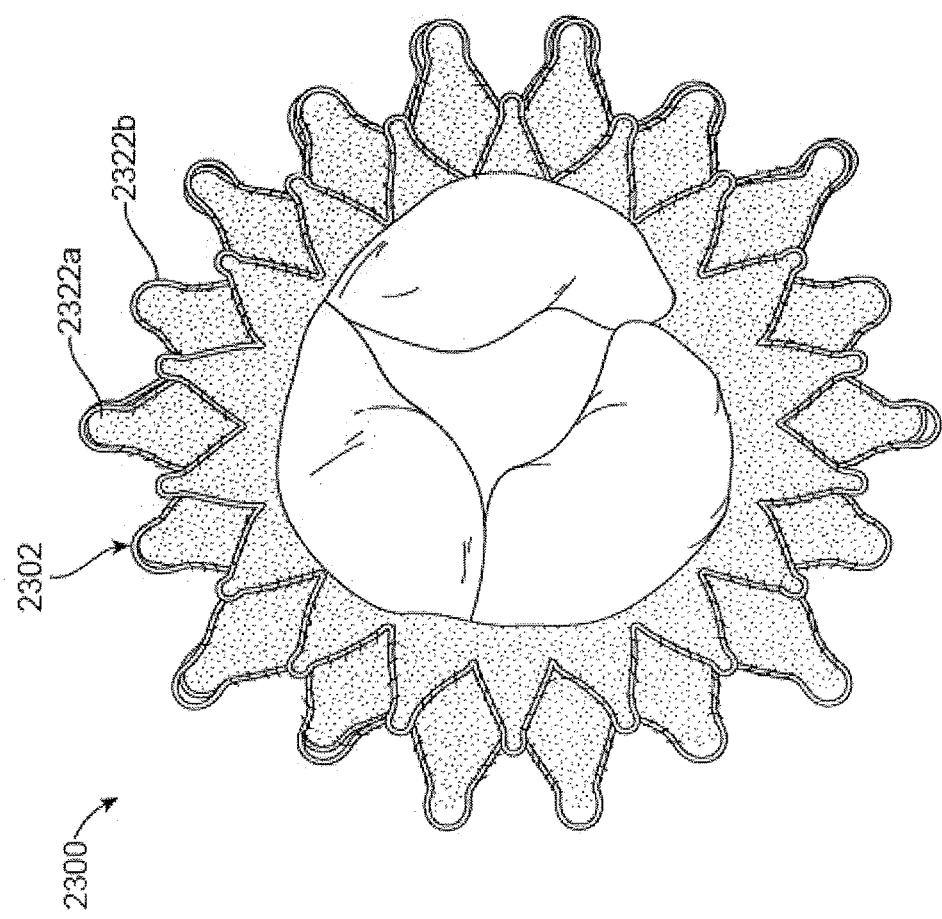
FIG. 4A is a top view of another embodiment of a valve prosthesis.
Figure 4B:
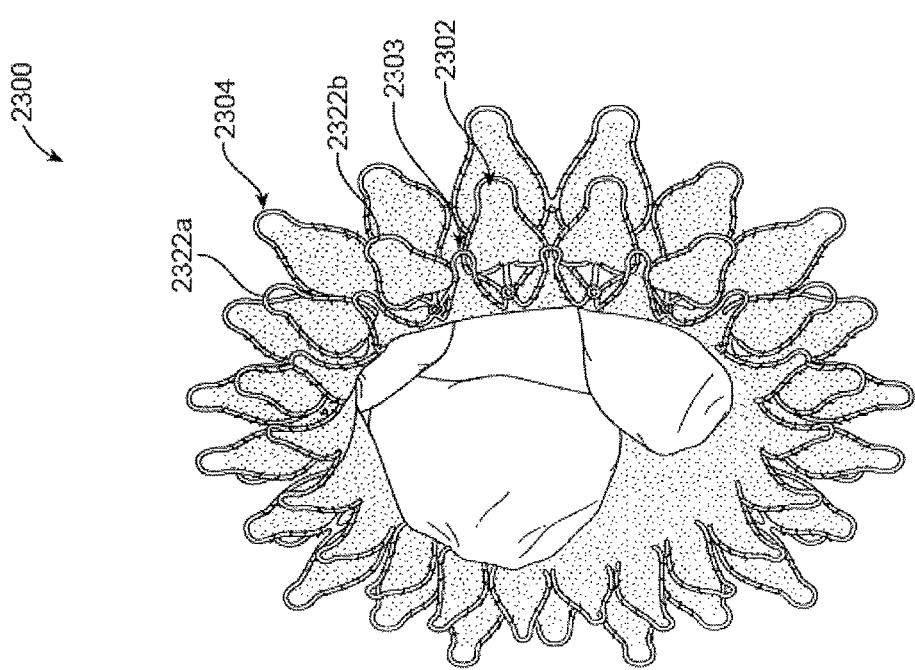
FIG. 4B is a side view of another embodiment of a valve prosthesis.
Figure 4C:
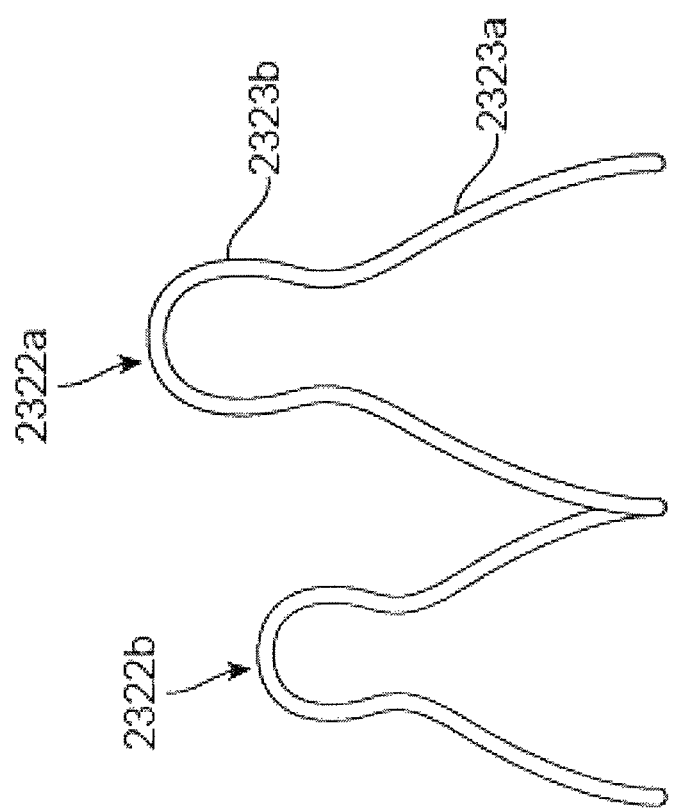
FIG. 4C is a close-up showing two anchor extensions side by side.

Referring to FIGS. 4A-4C, in some embodiments, one or both of the atrial and ventricular anchors 2302, 2304 of an expandable anchor of a replacement valve 2300 can include petals or extensions 2322a,b (only two are labeled for clarity) that are pear-shaped. That is, each extension 2322a,b can included two bulbous or rounded portions 2323a, 2323b. The radial innermost rounded portion 2323a can have a greater diameter than the radial outermost portion 2323b. The radial innermost rounded portion 2323a can be approximately 5-6 mm in diameter while the radial outermost portion 2323b can be approximately 2-3 mm in diameter. The pear-shaped extensions 2322a can advantageously provide sufficient grabbing force while providing a large-diameter blunt radial edge to reduce the chances of tissue damage.

Figure 4D:
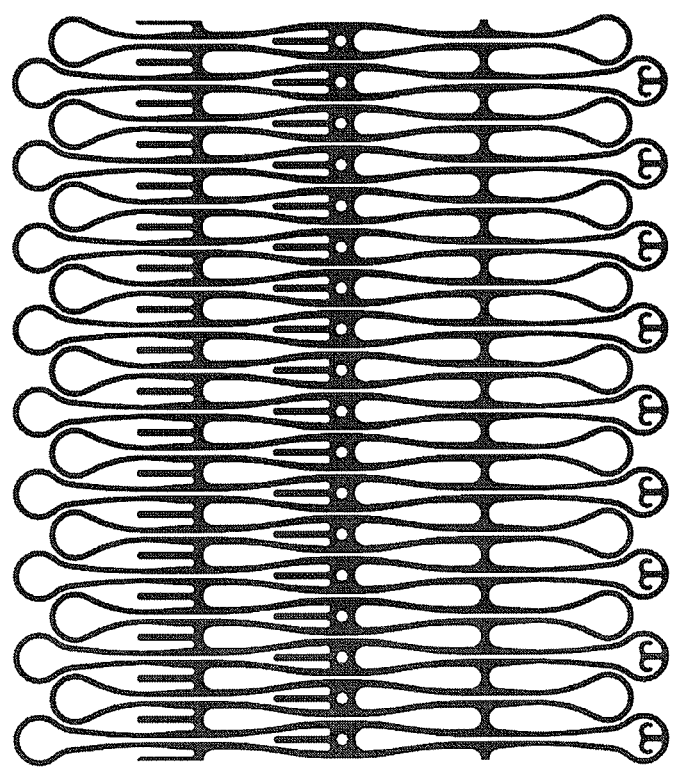
FIG. 4D shows a flattened anchor assembly.
Figure 5:
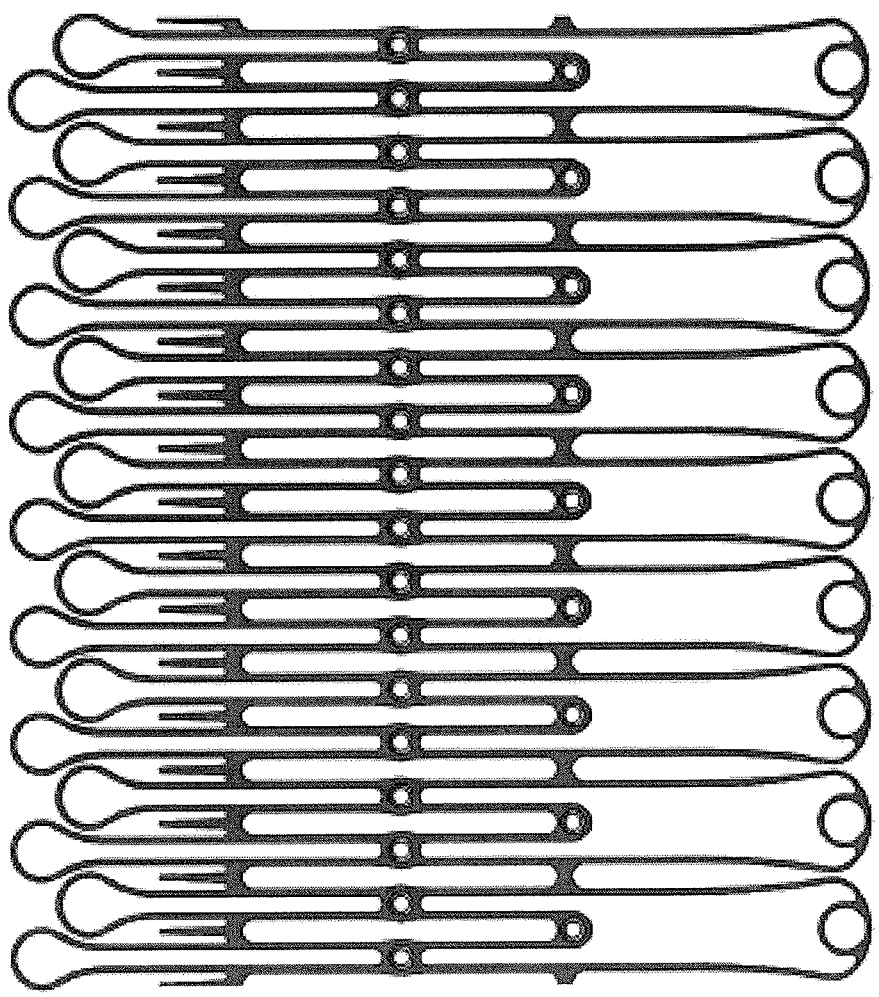
FIG. 5 shows another embodiment of a flattened anchor assembly.

Referring still to FIGS. 4A-4C, in some embodiments, the extensions 2322a,b can have varying radial lengths. For example, the anchor can include alternating longer extensions 2322a and shorter extensions 2322b around the circumference. The longer extensions 23222a, for example, can have a length that is 1-3 mm longer than a length of the shorter extensions 2322b. Having varying lengths can advantageously allow the extensions 2322a, 2322b to be cut out of a single tube or piece of material while still providing a large-diameter blunt radial edge. For example, FIG. 4D shows a pattern for the expandable anchor 2301 cut out of a flat piece of material (which would then be rolled to form the anchor 2301). In this pattern 2301, the atrial side includes double hooks therein for attachment to a delivery system, which will be described further below. FIG. 5 shows a similar pattern for an expandable anchor 5301 cut out of a flat piece of material. The expandable anchor 5301 includes alternating pear-shaped extensions only on the ventricular side of the anchor 5301.

Figure 7:
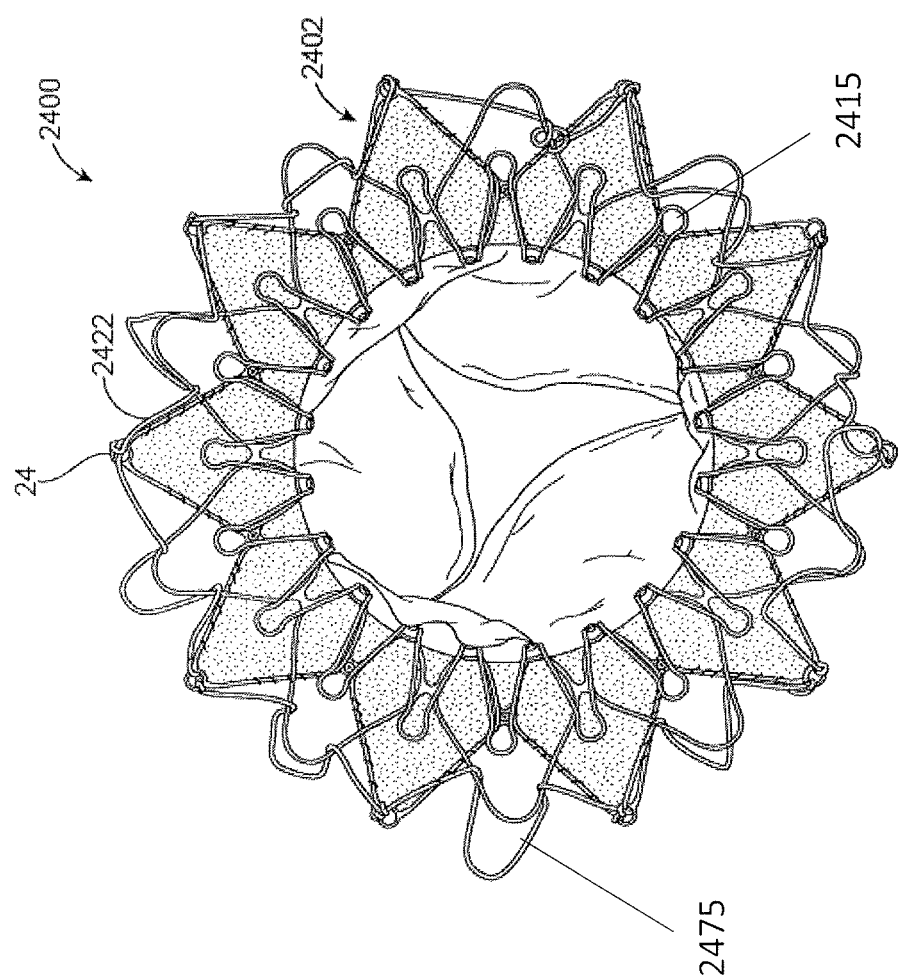
FIG. 7 shows a top view of another embodiment of a valve prosthesis.

In some embodiments where the alternating pear-shaped extensions are only on the ventricular side, the atrial side can include overlapping extensions that are substantially semi-circular in shape, as shown in FIGS. 2 and 7. In other embodiments, the anchor with the pear-shaped extensions can be used on both the ventricular and atrial side. In yet other embodiments, the anchor with the pear-shaped extensions can be used only on the atrial side. Moreover in some embodiments, the pear-shaped extensions can be arranged in an overlapping fashion.

Figure 6A:
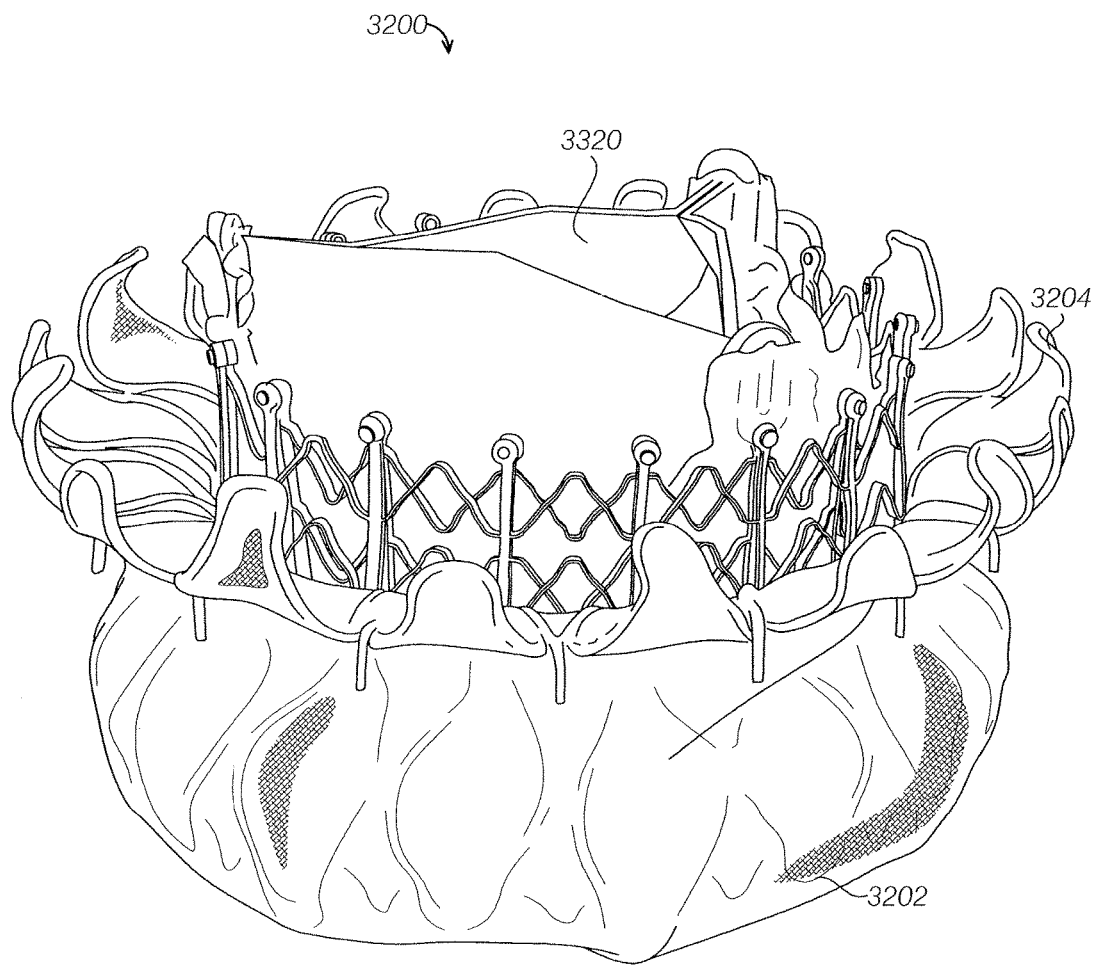
FIG. 6A shows another embodiment of a valve prosthesis.
Figure 6B:
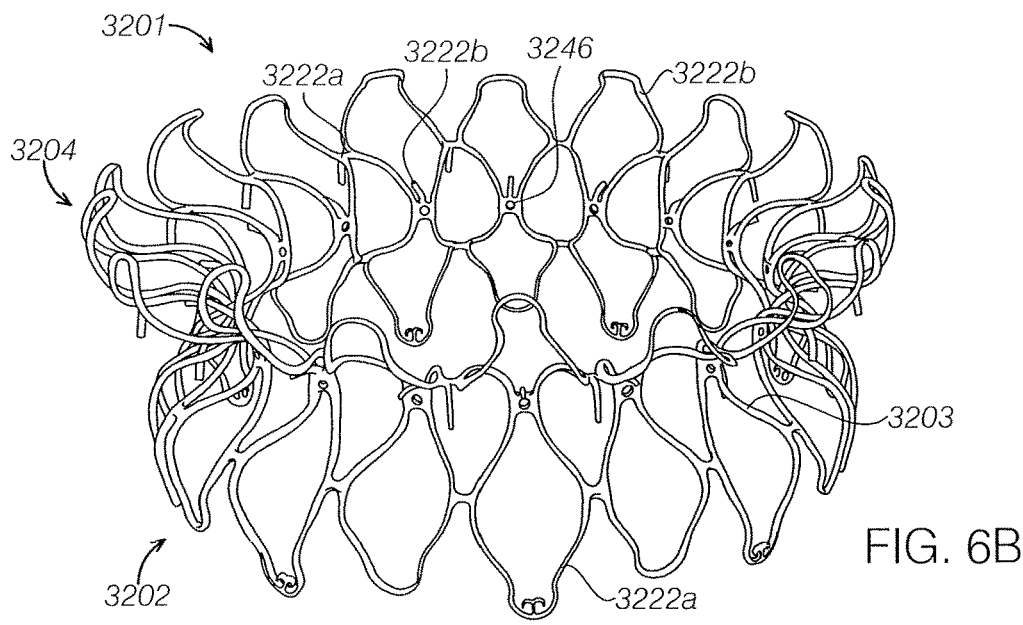
FIG. 6B shows the anchor assembly of the valve prosthesis of FIG. 6A.
Figure 6C:
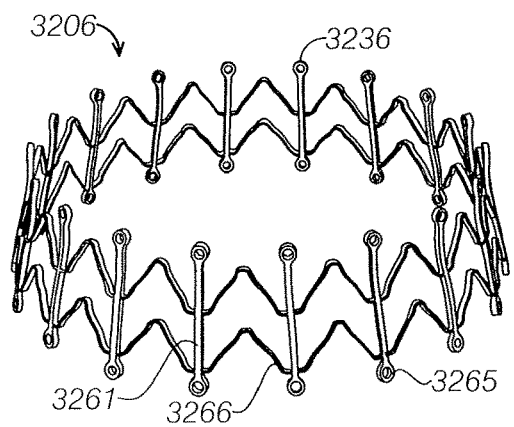
FIG. 6C shows a central member of the valve prosthesis of FIG. 6A.
Figure 6D:
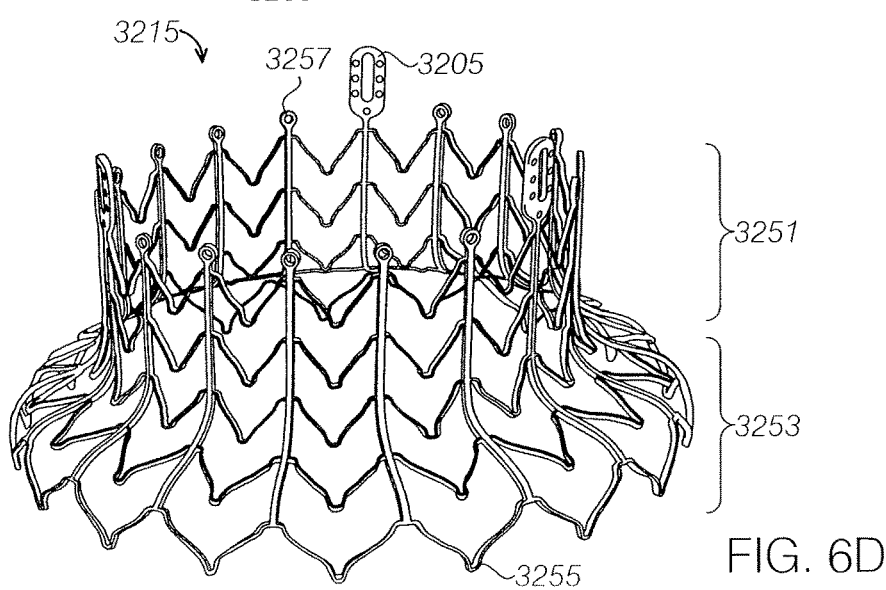
FIG. 6D shows a strut frame of the valve prosthesis of FIG. 6A.
Figure 6E:
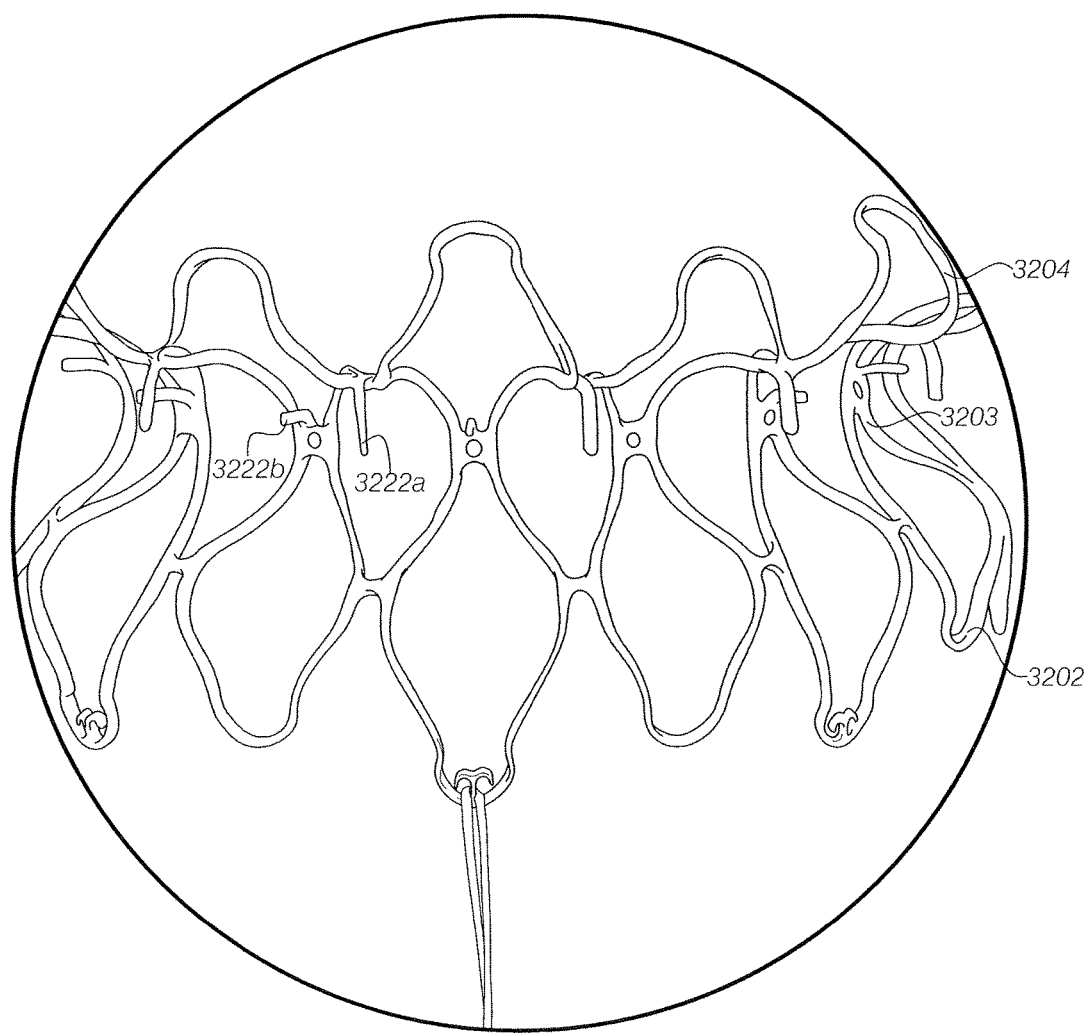
FIG. 6E shows a close-up of the anchor assembly of FIG. 6B.
Figure 6F:
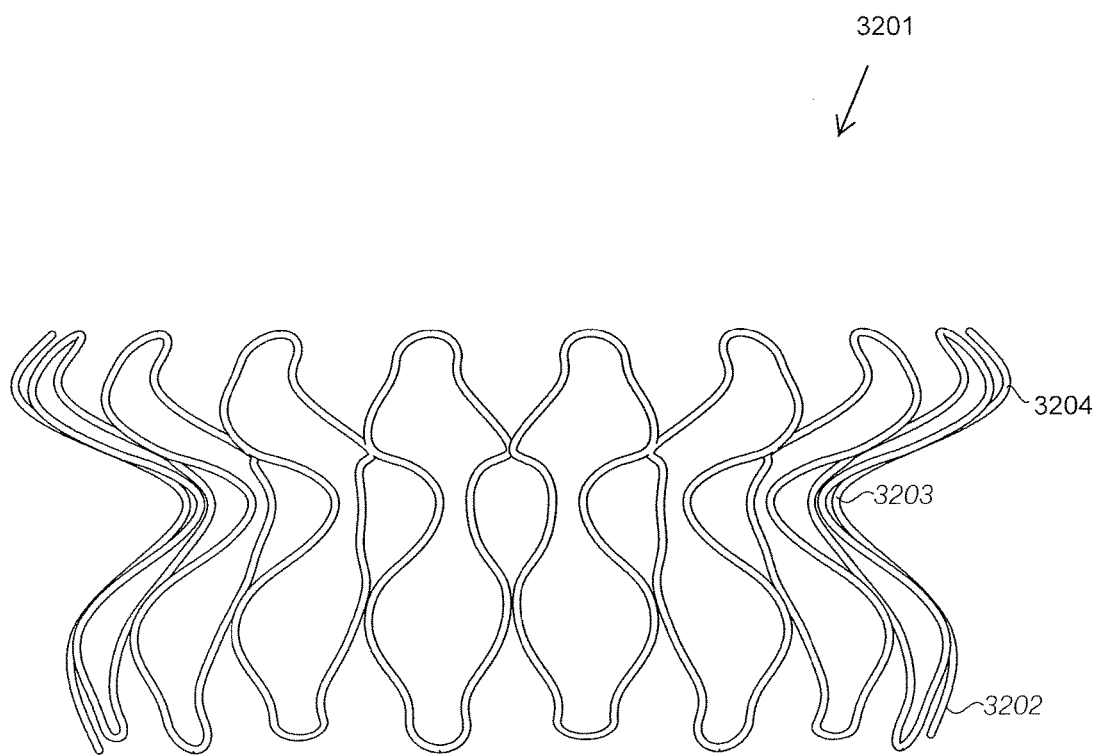
FIG. 6F shows a side view of the anchor assembly of FIG. 6B.

FIGS. 6A-6G show another embodiment of a replacement valve 3200 including an atrial anchor 3202 and ventricular anchor 3204. The atrial and ventricular anchors 3202 extend radially outwards relative to the central portion 3203. The extensions 3222a,b of the atrial anchor and of the distal anchor are both pear-shaped and of alternating lengths, as described above with respect to valve 2300. Further, the expandable anchor 3201 (including atrial anchor 2302, ventricular anchor 3204, and central portion 3203) forms a substantially hour-glass shape when viewed from the side, as can best be seen in FIGS. 6F and 6G). Referring to FIG. 6G, the atrial anchor 3202 extends radially outwards at an angle α (relative an axis 3297 parallel to an axis of the plane of the annulus (perpendicular to the central longitudinal axis 3299)) of between 20 and 30 degrees, such as approximately 25 degrees. The tips of extensions 3222a,b of the atrial anchor are then bent or curved such that they point substantially in the atrial direction when implanted. Likewise, the ventricular anchor 3204 extends radially outwards at an angle B (relative an axis 3298 parallel to an axis of the plane of the annulus (perpendicular to the central longitudinal axis 3299)) of between 5 and 20 degrees, such as approximately 10 degrees. Further, the tips of extensions 3222b of the ventricular anchor are bent or curved such that they point at least partially in the ventricular direction. Moreover, the tips of the ventricular anchor 3222b continue curving at least partially radially inwards. The radius of curvature R of the tips of the ventricular anchor 3204 can be approximately 0.1 inches to 0.2 inches, such as ⅛ inches. Having the tips extensions 3222b of the ventricular anchor 3204 curve around to point radially inwards advantageously keeps the tips from getting caught on material, such as cords, in the ventricle during implantation. Further, having the tips extensions 3222a of the atrial anchor point substantially in the atrial direction advantageously provides a funnel to enhance flow of blood from the atrium to the ventricle (i.e., without interrupting the flow or providing pockets for the blood to pool therein).

In some embodiments, one or more of the anchors can have holes, eyelets, or other attachments mechanisms therein to allow a delivery device to attach thereto to control placement of the replacement valve. Exemplary delivery devices and methods are described in International Patent Application filed May 13, 2016, titled "CARDIAC VALVE DELIVERY DEVICES AND SYSTEMS," the entirety of which is incorporated by reference herein. Referring to FIGS. 6B and 6E, one or more of the anchors (here atrial anchor 3202) can include double eyelet hooks 3224 positioned in the distal tip of the extension 3222a of the atrial anchor 3202. The eyelets 3224 advantageously allow tethers from the delivery device to hold the atrial loops in a retracted position. The outer radial positioning of the eyelets 3224 can advantageously allow the tethers to pull the loops tightly into the sheath. Further, the double eyelet hooks can advantageously make it easy for an operator to loop the tether therethrough (as shown in FIG. 6E).

Another embodiment of an eyelet 24 for delivery is shown in FIG. 7. Eyelet 24 is a full circle that allows a suture to be passed therethrough. The eyelets 24 are positioned at the peak or furthest radial position of the extensions 2422 on the atrial anchor 2402. The suture 2475 looping around the circumference of the anchor 2402 and through the eyelets 24 can help prevent the atrial anchor 2402 from flaring outwards during delivery.

In some embodiments, the eyelets can be only on the extensions of the atrial anchor. In other embodiments, the eyelets can be only or additionally on extensions of the ventricular anchor. As shown in FIGS. 6E and 7, the eyelets can be positioned along every other extension around the circumferential direction (such as only one of the overlapping frames, as shown in FIG. 7). In other embodiments, the eyelets can be positioned on every extension of the atrial or ventricular anchors.

The expandable anchors described herein can further include one or more apertures or holes configured for coupling attachment of various pieces of the valve. For example, referring to FIG. 6B, the expandable anchor 3201 can include a plurality of apertures 3246 therein configured to allow attachment via a coupler, such a rivet, to other sections of the valve, as described further below.

The prostheses herein also include struts or a strut frame, to which the replacement leaflets are attached for controlling blood flow through the valve. There can be three strut leaflets, which can form a pressure actuated valve that provides uni-directional flow occlusion when the prosthesis is implanted in the valve orifice. The leaflets can be constructed of bio-materials, such as bovine or porcine pericardium, or polymer materials.

Some central portions herein or other portions of other replacement heart valves may be susceptible to undesirable deforming when implanted, such as due to movement during the heartbeat and/or in response to pressures in the heart. The valves described herein can thus include a separate annular strut frame coupled to a radially inner portion of the central portion (i.e., within the central portion). The annular strut frame may distribute forces more evenly over the central portion of the expandable anchor and may reduce the likelihood of undesirable central portion deformation once implanted.

An annular strut frame is an additional layer of material secured to the radially inner portion of the central portion, which reinforces and stabilizes the central portion when implanted. Additionally, by creating a coupling between the struts and the central portion (as opposed to having a solid portion of material that can provide additional stability), the flexibility of the coupling allows for relative movement of the struts during collapse of the device. This can reduce stresses on the device as it is collapsed, allowing for a smaller delivery profile, which as discussed herein can be important for delivery, such as a transseptal approach. The term annular in this context does not require a perfect annulus.

When the prosthesis includes a strut frame, the struts can either be integral to the strut frame or they can be separate components that are secured to the strut frame during manufacturing.

Figure 8:
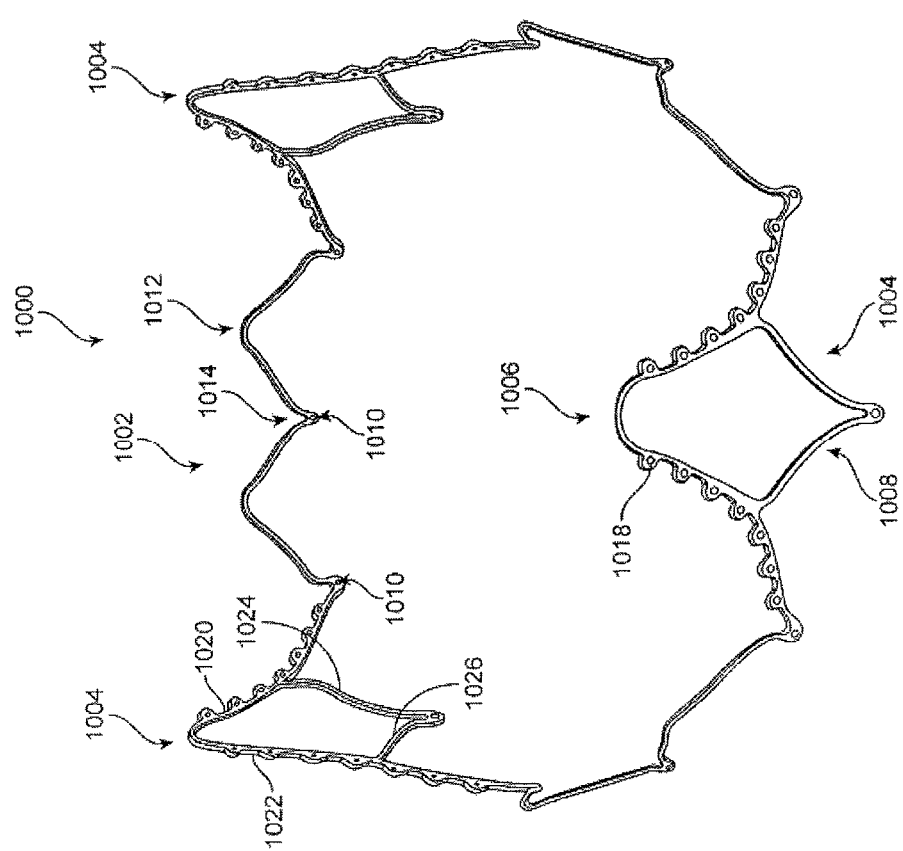
FIG. 8 shows an embodiment of a strut frame.

FIG. 8 is a perspective view illustrating an exemplary annular strut frame 1000. Strut frame 1000 includes frame portion 1002 and plurality of struts 1004. Struts 1004 extend further distally (i.e., in the ventricular direction) than frame portion 1002, and are configured to be secured to replacement leaflets as described herein. The strut frame 1000 has a ventricular end 1006 and an atrial end 1008. Strut portion 1002 includes a plurality of arches, which define peaks 1012 and valleys 1014. In this embodiment there are six strut frame arches, with two between adjacent struts 1004. Struts 1004 have an arch configuration defined by first leg 1020 and second leg 1022, each of which has a plurality of suture apertures 1018 therein. Struts 1004 each also have first and second extensions 1024 and 1026 extending away from legs 1020 and 1022 and towards atrial end 1008. Extensions 1024 and 1026 may also be considered part of the frame portion rather than the struts. Replacement leaflets are secured to struts 1004 at holes 1018 (e.g., by suturing). The strut frame also includes a plurality of apertures 1010 near the atrial end 1008, which are used to secure the annular strut frame to the central portion of the expandable anchor. The apertures are located at valleys 1014 in the frame portion. In some embodiments the annular strut frame is positioned radially within the central portion so that each of apertures 1010 is aligned with an aperture in the central portion, such as apertures 36. A coupler (e.g., rivet) is then advanced through the aligned apertures and one side of the coupler is then plastically deformed to secure the annular strut frame to the central portion.

Figure 9:
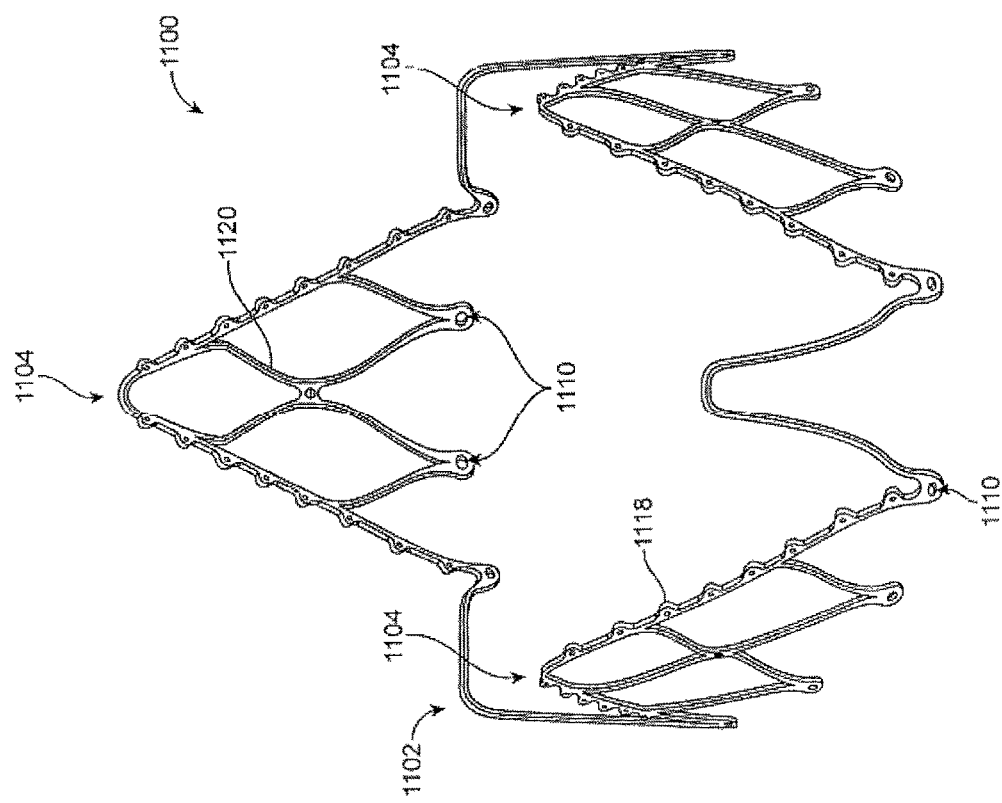
FIG. 9 shows another embodiment of a strut frame.

FIG. 9 illustrates an exemplary annular strut frame 1100. Strut frame 1100 includes three struts 1104 and frame portion 1102, which in this embodiment includes one arch between adjacent struts 1104. Unlike the embodiment in FIG. 8, in which there is one coupling aperture 1010 within each strut, in this embodiment there are two apertures 1110 within each strut 1104. Just as in the embodiment in FIG. 8, there are also apertures at the ends of each leg of struts. Strut frame 1100 is coupled to a central portion by aligning apertures 1110 with apertures in the central portion, such as aperture 36, and then extending a coupler through each set of aligned apertures, and plastically deforming each coupler to secure the central portion to the annular strut frame at the locations of the couplings.

FIGS. 8 and 9 illustrate exemplary strut frames in their expanded configurations, when the rest of the expandable anchor (e.g., ventricular anchor, central portion, and atrial anchor) is also in an expanded configuration. Strut frames 19 and 20 can be secured to, and considered part of, any of the expandable anchors herein.

In an exemplary method of manufacturing, the strut frame is cut from a tubular element, then expanded, and set in the expanded configuration using shape setting techniques described herein or otherwise known. For example, in an exemplary embodiment, the frame is cut from a 10 mm diameter tube, then expanded to an expanded configuration of about 32 mm (as shown in FIG. 19), and set in the expanded configuration. In some exemplary embodiments the strut frames herein are 0.25 mm to about 0.45 mm thick, such as about 0.35 mm thick.

The annular strut frame can be cut from a flat sheet and rolled up and secured together (examples of which are described above), or it can be cut from a tubular structure.

FIGS. 8 and 9 illustrate exemplary annular, or cylindrical, strut frames can be disposed radially within the central portion of the expandable anchor. The central portion and the strut frame can be thought of as creating a composite cylinder when they are coupled together. The composite cylinder is thicker than each of the central portion and strut frame individually. Each of the central portion and strut frame is, however, relatively thin and can flex with respect to the other component. The relative flexibility can make it easier to collapse into a delivery configuration. If the composite region were a single material with a thickness equivalent to the combined thickness of the central portion and strut frame, that modified region may not be able to collapse sufficiently to meet, for example, size constraints without overstraining. The central portion and strut frame acting as a composite structure will not overstrain when collapsed into a collapsed configuration since the central portion and strut frame can flex independently. The composite central portion and strut frame also, when the expandable anchor expands, has a thickness greater than each component individually, thus providing an increased thickness that may be needed to resist torqueing and other forces on the central portion when implanted. The composite central portion and cylindrical strut frame thus enables collapsing as needed without overstraining, as well as provides a thickness to the central region that resists torqueing and deformation due to forces acting on the expandable anchor when implanted.

FIGS. 10A-E illustrate another exemplary annular or cylindrical strut frame 2500 that can be disposed radially within the central portion of the expandable anchor. As shown, strut frame 2500 can include a frame portion 2502 at the atrial end 2508 and a plurality of struts 2504, such as three struts 2504, at the ventricular end 2506. While the frame portion 2502 can extend substantially around the entire valve, the struts 2504 can extend at discrete locations about the valve. For example, the midpoint or center of each of the struts 2504 can be positioned approximately 120° away from one another.

The entire frame 2500 can be made of a plurality of substantially diamond-shaped sub-features 2551 arranged in a pattern. The diamond sub-features 2551 can advantageously provide structural support to the strut frame 2500 and can be substantially resistant to deformation when circumferential and/or axial forces are placed on the strut frame 2500.

The atrial-most tips 2553 of the strut frame 2500 can be rounded or blunt to prevent damage to the tissue when implanted. Moreover, as shown in FIGS. 10A-D, the atrial tips 2553 of the strut frame can be flared radially outwards relative to the rest of the strut frame 2500, which can remain substantially cylindrical. The angle of the bend can be between 25 degrees and 30 degrees relative to a plane of the annulus (i.e., 60-65 degrees relative to the central vertical axis of the annulus). Further, the atrial trips can substantially conform to the angle of the atrial anchor relative to the central portion. A similarly flared structure can be seen in the strut frame 2415 of FIG. 7.

Referring still to FIGS. 10A-10D, the struts 2504 can each be substantially triangular in shape with blunt tips formed from three substantially aligned diamond sub-features (labeled as 2551a,b,c,d on FIG. 25B). The middle diamond sub-feature 2551b of each strut 2504 can include one or more eyelets 2555 formed as a sewing attachment point for the leaflets. Likewise, one or more of the diamond sub-features 2551 can include eyelets 2557 for attachment of the leaflets.

The strut frame 2500 can further include apertures 2510 that can be used as rivet holes for attachment to the anchor frame. The apertures 2510 can be positioned, for example, between the proximal-most diamond sub-features 2551 of the strut frame 2500.

FIG. 10D shows the same strut frame 2500 in a two-dimensional un-stretched configuration. To form the strut frame 2500 in the three-dimensional configuration shown in FIGS. 25A-25D, the two-dimensional version can be stretched linearly (in the direction shown by the arrows on FIG. 30), and the atrial end 2408 can be bent. Advantageously, the strut frame 2500 can be cut out of a single piece of material, such as a tube or a flat sheet. The strut frame 2500 can be approximately 12-15 mm high and 27-32 mm in diameter.

Referring to FIGS. 11A-B, the radial flare of the tips 2633 at the atrial end 2608 of the strut frame 2615 can allow the atrial end 2608 to sit substantially flush with the atrial anchor 2602. The tips 2633, however, can remain unattached to the atrial anchor 2602 in order to allow for ease of collapse.

Figure 12B:
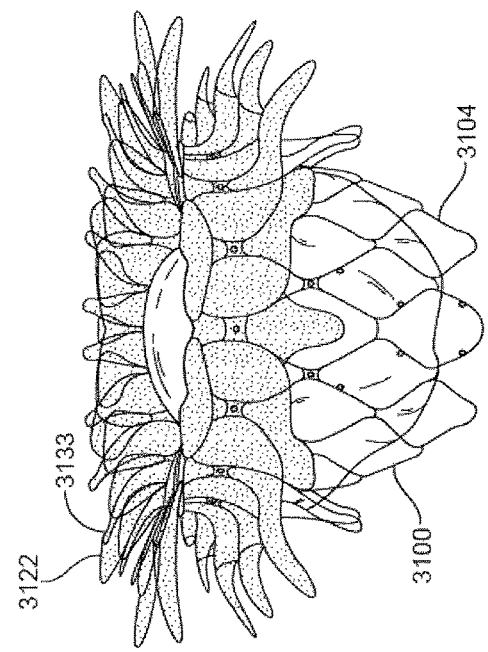
FIGS. 12A-12B show another embodiment of a valve prosthesis.
Figure 12A:
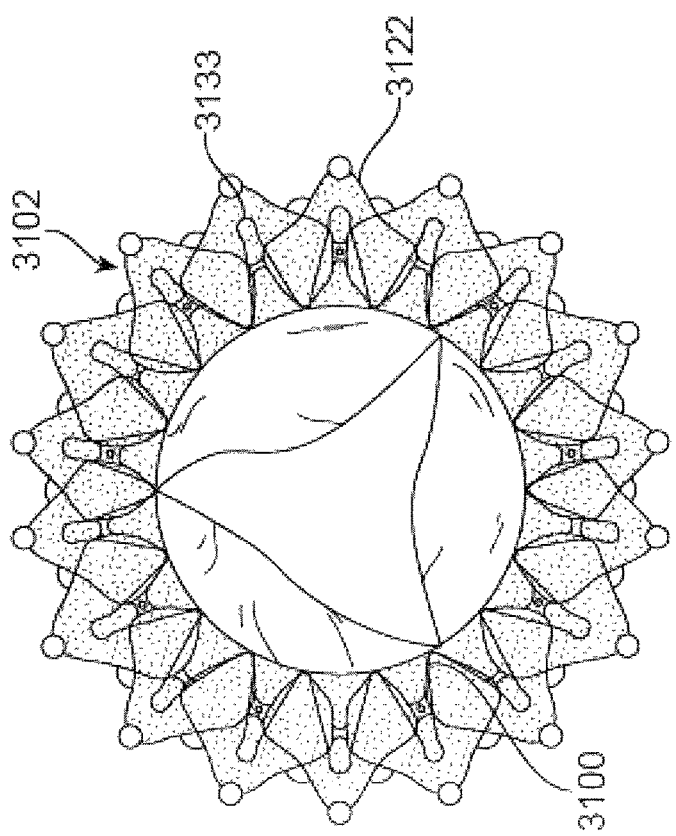

In some embodiments, as shown best in FIG. 12A, the atrial tips 3133 of the strut frame 3100 can be axially aligned with the extensions 3122 of the atrial anchor 3102. That is, the midline of each tip 3133 can align with the midline of each extension 3122. The strut frame 3100 can be attached to the anchor 3100, such as a rivet extending between apertures 2510 (see FIGS. 10A-10D) and apertures formed in the central portion of the anchor. Further, as shown in FIG. 12B, the atrial tips 3133 substantially conform to the angle of the atrial anchor 3102, forming a continuous or smooth funnel from the proximal end to the distal end. The smooth funnel can advantageously ensure that blood flowing therethrough will flow continuously without catching or pooling within portions of the device, thereby preventing the formation of blood clots. Moreover, as further shown in FIG. 12B, the strut frame 3100 can be positioned such substantially all of the struts 3104 extend distally past the ventricular anchor 3104.

Another embodiment of a strut frame 3215 is shown in FIG. 6D. As shown in FIG. 6D, the strut frame 3215 includes a substantially cylindrical ventricular portion 3251 and a flared atrial portion 3253 extending at least partially radially away from the cylindrical ventricular portion 3251. The flared atrial portion forms an angle of approximately 25-30 degrees relative to a plane of the annulus (i.e., 60-65 degrees relative to the central vertical or longitudinal axis of the annulus). Further, in this embodiment, the atrial tips 3255 of the flared atrial portion curve back to point substantially in the axial direction (similar to the atrial anchor 3201). Thus, referring to FIG. 6A, when placed within the atrial anchor 3201, the flares and atrial tips of each will be substantially flush with one another.

Referring to FIG. 6D, the strut frame 3205 includes a plurality of zig-zag circumferential members extending around the circumference of the frame and a plurality of linear members extending from the ventricular end to the atrial end. Further, a plurality of eyelet apertures 3257 are positioned at the ventricular side. The eyelet apertures can be used to connect the strut frame 3215 to the anchor assembly 3201, such as via couplers or rivets.

In some embodiments, the strut frame 3205 can include a suture woven circumferentially around the strut frame 3205 (such as through the zig-zag members), similar to as shown in FIG. 7. The suture can advantageously help maintain the shape of the strut frame 3205 during delivery (e.g., help prevent flaring) so as to maintain low stress on the leaflets during delivery.

As shown in FIG. 6D, the strut frame 3215 further includes ovoid attachment features 3205 at the ventricular end of the frame 3215 (attached leaflets 3220 are shown in FIG. 6A). The ovoid attachment features 3205 include a plurality of sutures holes therein for attachment of the leaflets. The ovoid shape can advantageously distribute stress evenly at the highest stress point of the leaflets. In one embodiment, there can be three ovoid attachment features 3205 separated approximately 120 degrees around the circumference from one another. In this embodiment, other portions of the leaflets can be sewn directly to the zig-zag and/or features of the strut frame.

Another mechanism for attaching leaflets is shown in FIGS. 13A-13B. Strut frame 4615 includes one or more eyelets 4655 extending along the strut frame for sewing attachment of the leaflets 4620.

The strut frames described herein can be configured to mechanically isolate the leaflets from the anchoring mechanism of the implant, thereby isolating the leaflets from stresses caused by movement of the annulus and/or the non-uniform shape of the annulus. In any of the embodiments described herein, the strut frame can have greater radial strength or rigidity than the anchor, thereby allowing the strut frame to retain its substantially cylindrical shape while the anchor conforms to surrounding anatomy. In one embodiment, the strut frame deflection under full pressure loading results in a 1-2 mm decrease in diameter.

In some embodiments, a central member or suspension can extend between the strut frame and the anchor frame. The central member can help provide further mechanical isolation of the leaflets relative to the anchoring members. That is, it is generally desirable that the strut frame to which the leaflets are attached maintain its intended expanded configuration. If the strut frame deforms too extensively, the orientation and/or alignment of the replacement leaflets that are secured to the strut frame can be compromised, which may prevent proper leaflet coaptation during use. The central member described herein prevents or at least minimizes movement or deformation of the expandable anchor from being translated to the strut frame. Alternatively stated, the central member reduces deformation of the strut frame in response to deformation of the expandable anchor. The central member can thus be thought of as a shock system between the expandable anchor and the strut frame (or the replacement leaflets). In response to deformation of expandable anchor, the central member is configured to deform while preventing or minimizing deformation of the strut frame.

Figure 14:
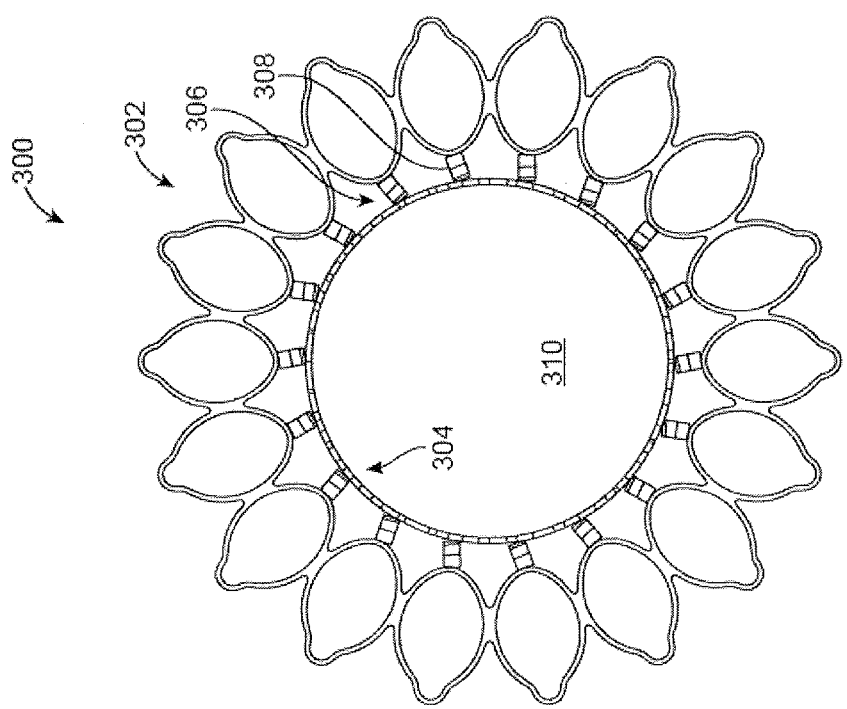
FIG. 14 shows a top view of a valve prosthesis having spring members between the strut frame and the anchor assembly.

FIG. 14 illustrates a mitral valve prosthesis 300 (viewed from a ventricular side) that includes a central member 306 in addition to the expandable anchor 302 and strut frame 304. The expandable anchor 302 is coupled to the central member 306, and the central member 306 is coupled to strut frame 304. Strut frame 304 defines central opening 310. Although shown as including non-overlapping pear-shaped petals or extensions, the expandable anchor 302 can be any of the expandable anchors described above or incorporated by reference herein. Further, strut frame 304 can be any of the strut frames described above. Moreover, in some alternative embodiments, the strut frame shown in FIG. 14 is replaced with discrete struts. The replacement leaflets that are secured to strut frame 304 are not shown in FIG. 14 for clarity.

As shown in FIG. 14, the central member 306 can include a plurality of connectors or spring elements 308 extending between the anchor 302 and the strut frame 308. The spring elements 308 can be resilient members that together act as a suspension for the strut frame 304 and can compress or extend when force is applied thereto, but can return to their former shape when released. The spring elements 308 can thus be used to absorb forces placed on the anchoring member to prevent or reduce forces on the strut frame (and thus the leaflets). The spring elements 308 can include leaflet springs (as shown in FIG. 14), S-springs (as shown in FIG. 15A), V-springs (as shown in FIG. 15B, circle springs (as shown in FIG. 15C), or any other type of spring elements, such as helical springs. In some embodiments, all of the spring elements 308 are the same type of spring, while in other embodiments, different types of springs can be used.

In the exemplary embodiment in FIG. 14, central member 306 includes eighteen individual or discrete spring elements 308. The spring elements 308 are secured to expandable anchor 302 at a radially outer end and to strut frame 304 at a radially inner end. Springs 308 can be secured to expandable anchor 302 and to strut frame 304, for example, via rivets, such as is described herein. As shown, in FIGS. 15A-15C each spring element 308 can include two apertures 3912 therein at opposite ends of the spring. The apertures 3912 can allow for attachment of the spring elements 308 to the strut frame and the anchor through rivets or other attachment mechanisms. The spring elements 308 can be secured to expandable anchor 302 along the central portion of expandable anchor 302, which is the radially innermost portion of expandable anchor 302.

In other embodiments, there may be few or more spring elements 308. For example, if the expandable anchor had a design different than shown in FIG. 14, fewer spring elements 308 may be needed. Or, alternatively, the design in FIG. 14 could have nine spring elements 308, leaving out every other spring element around the strut frame 304. Alternatively, the implant can have four spring elements 308 disposed about every 90 degrees around the strut frame 304, or three spring elements 308, or even two spring elements 308. The implant can have, for example, inclusively, between 1 and 25 springs, such as between 1 and 20 spring elements, such as between 2 and 20 spring elements. In some embodiments, different spring elements 308 of the suspension 306 can have different spring constants. The spring constants can be between 20 g/mm and 100 g/mm.

Figure 16A:
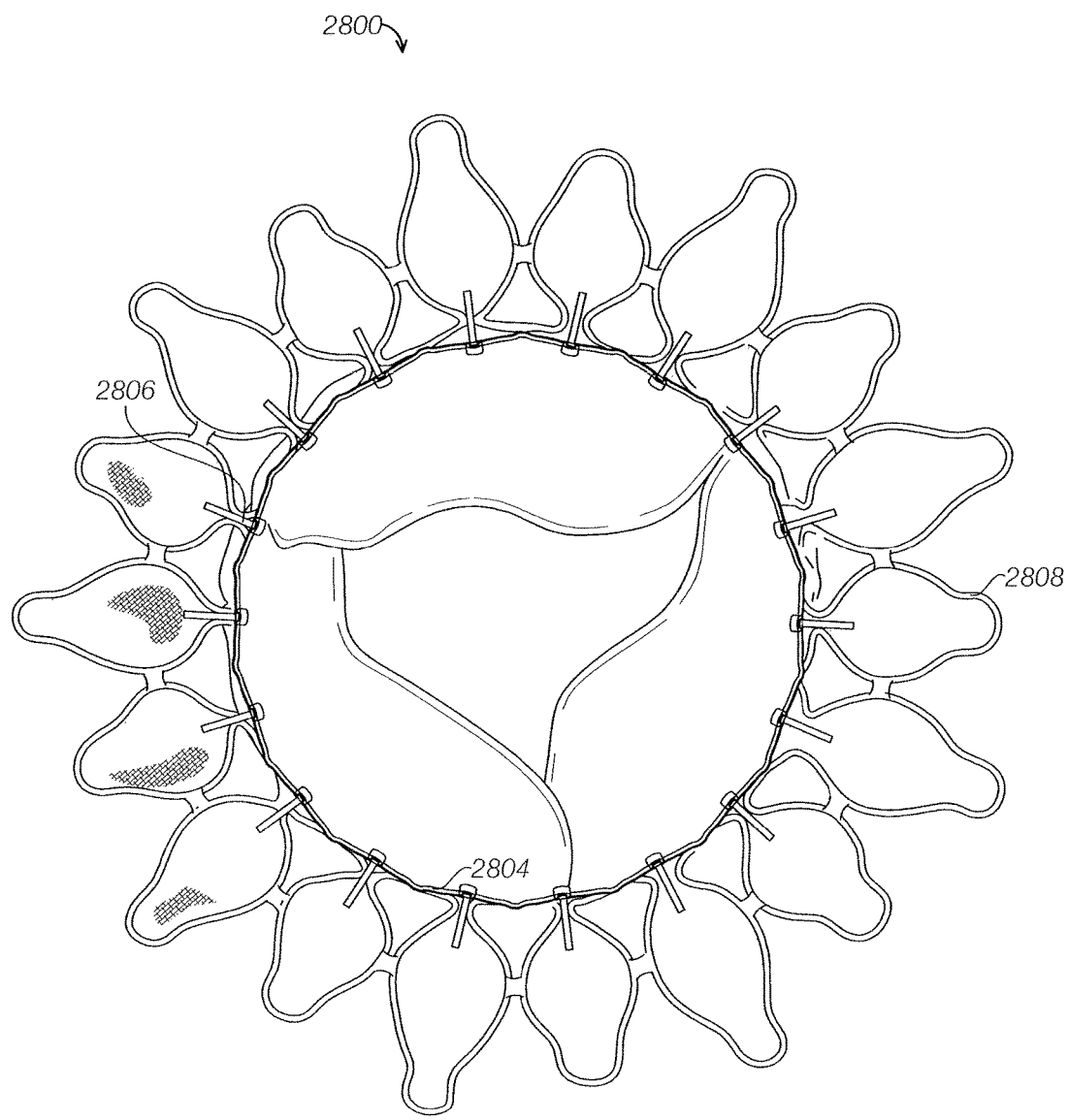
FIG. 16A-16C show another embodiment of a valve prosthesis.
Figure 16B:
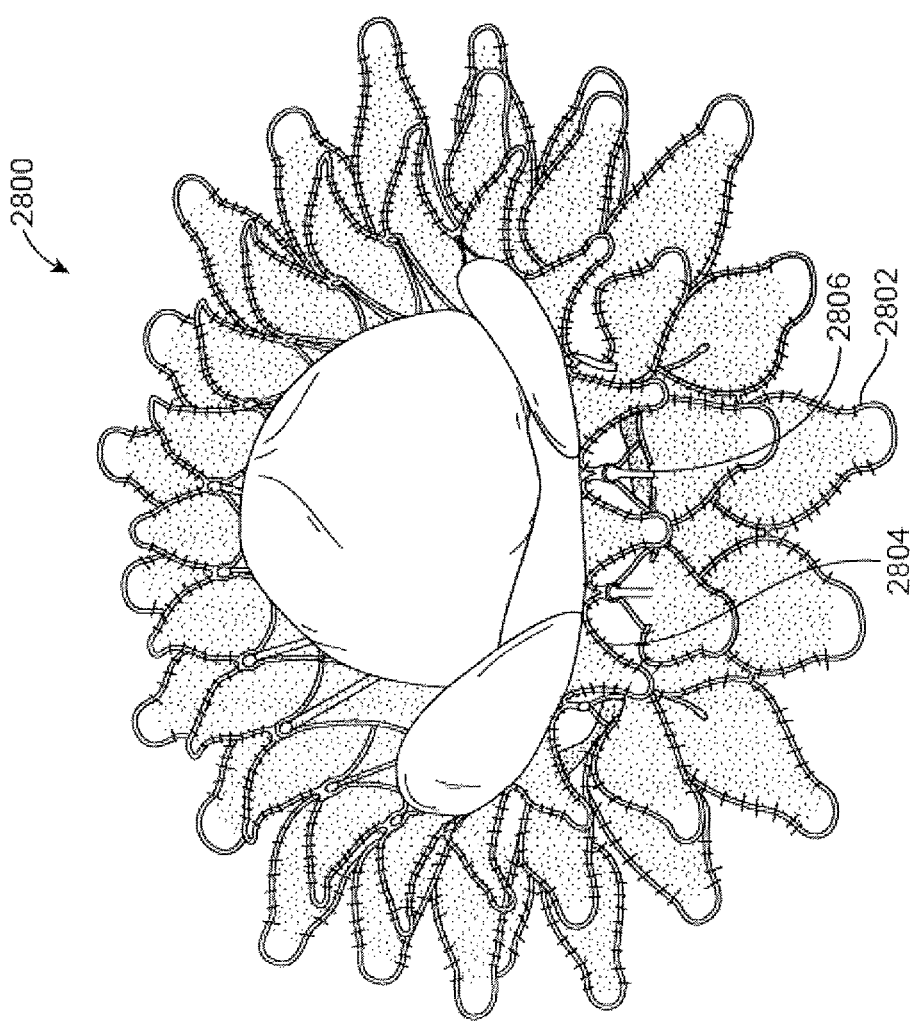
Figure 16C:
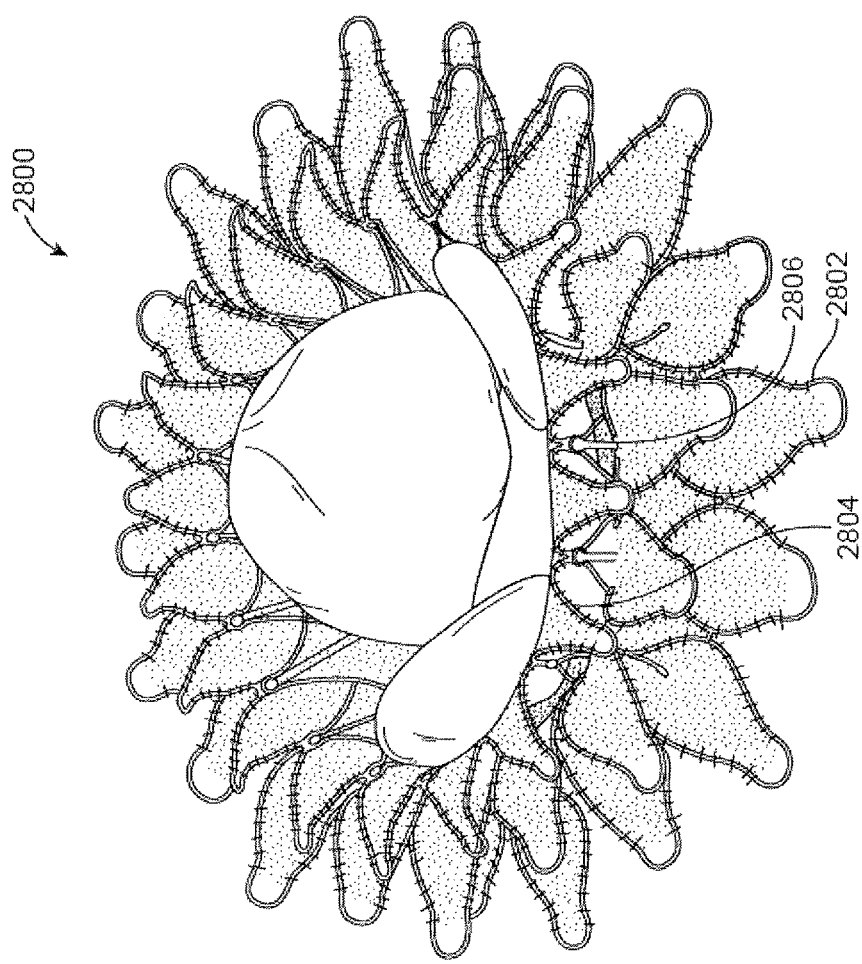
Figure 17A:
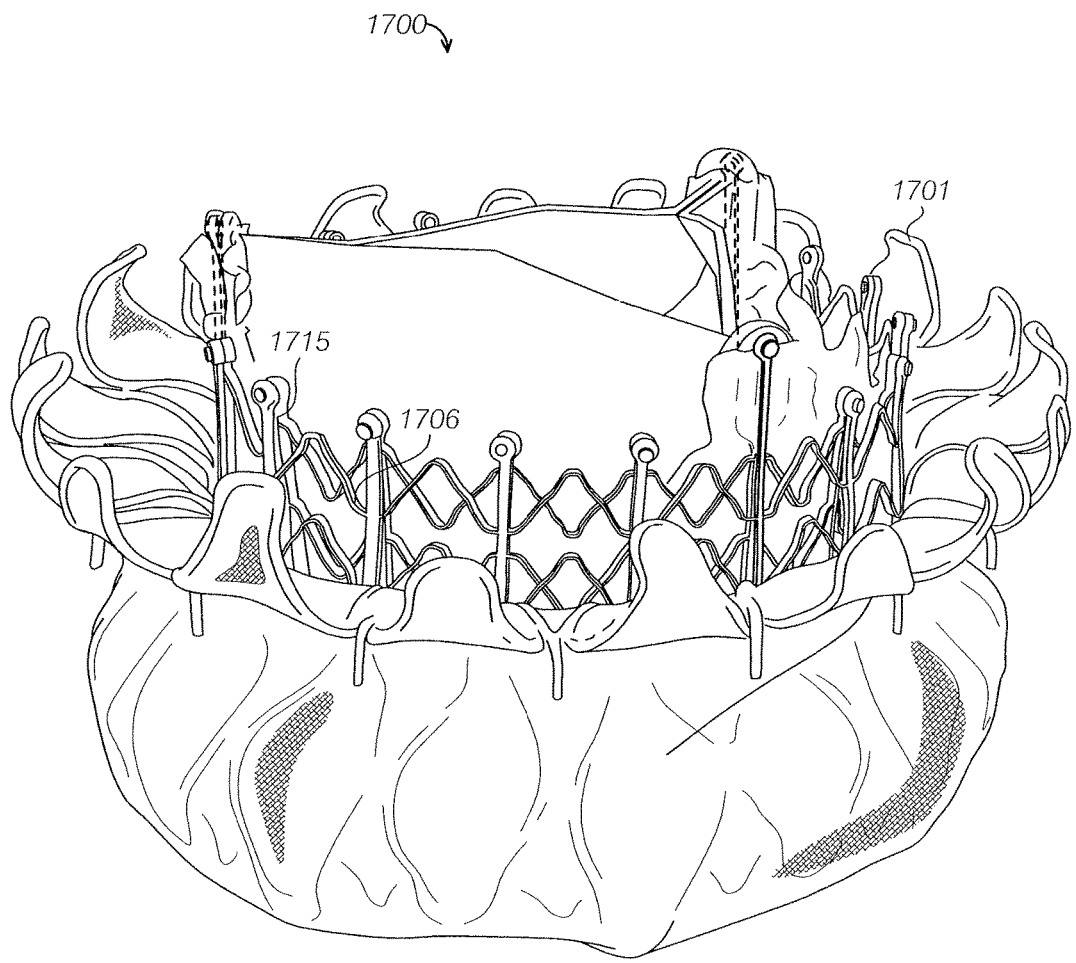
FIG. 17A shows another embodiment of a valve prosthesis.
Figure 17B:
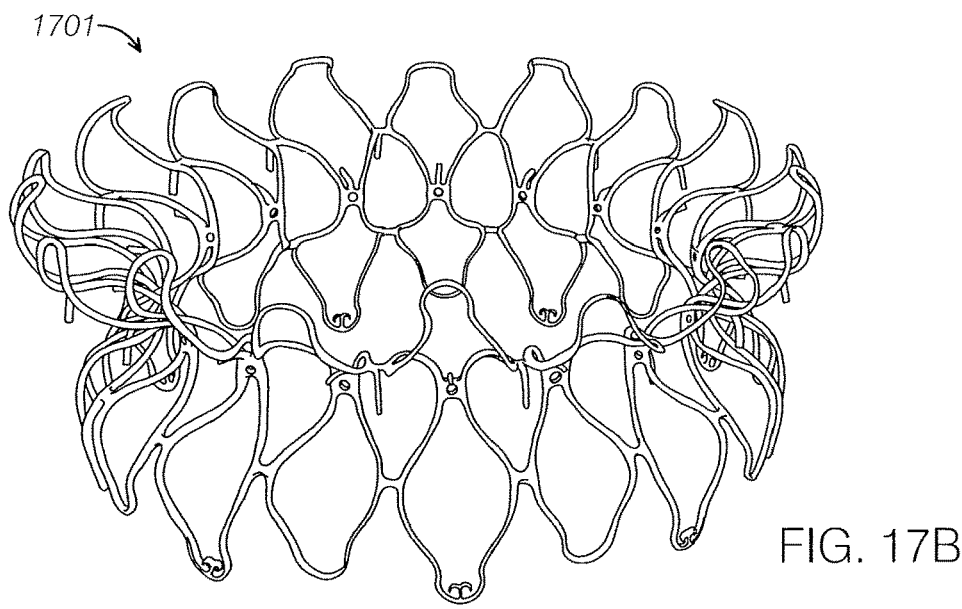
FIG. 17B shows the anchor assembly of the valve prosthesis of FIG. 17A.
Figure 17C:
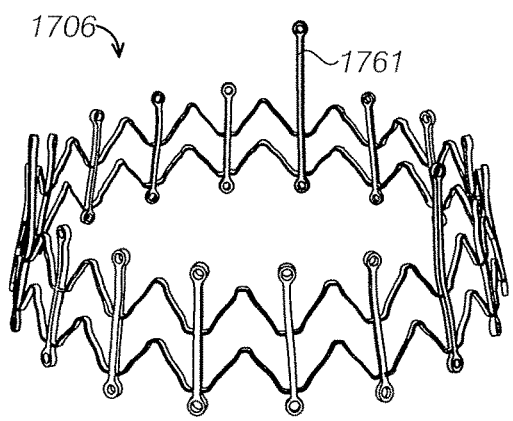
FIG. 17C shows the central member of the valve prosthesis of FIG. 17A.
Figure 17D:
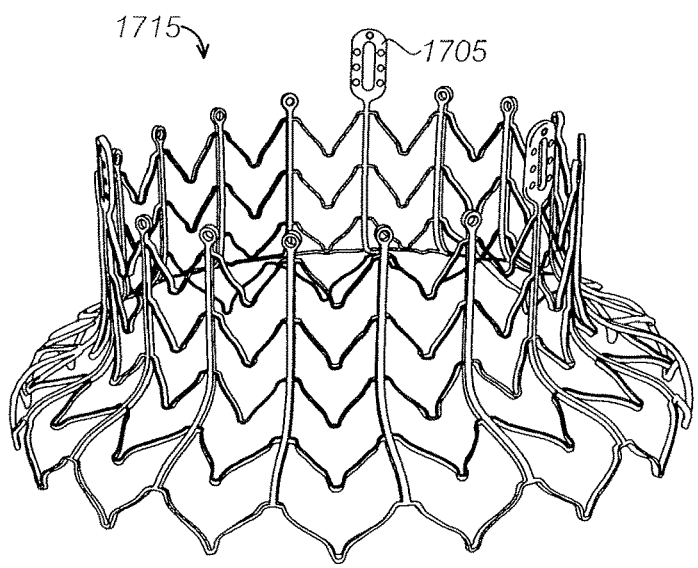
FIG. 17D shows the strut frame of the valve prosthesis of FIG. 17A.

FIGS. 16A-C show a mitral valve prosthesis 2800 including an outer expandable frame 2804, a central member 2806 (in the form of a plurality of individual spring elements), an annular strut frame 2802, and leaflets. As can be seen in FIGS. 16A-16C, the radially inner strut frame 2804 is radially offset from the outer expandable frame 2802 due to the central member or 2806.

In some embodiments, the central member can have a continuous annular configuration, such as form a continuous spring 2908, as shown in FIG. 15D, configured to extend around the entire circumference of the strut frame 304 (i.e., between the strut frame 304 and the anchor 302). The continuous spring can have a plurality of bends that act as springs and a plurality of apertures 2911, 2933 arranged in an alternating configuration such that neighboring apertures 2911, 2933 attach to the strut frame and the anchor assembly. As shown in FIG. 15D, the continuous spring can be attached such that at least one bed extends between the strut frame and the anchor frame, providing an offset (and additional spring element) between the two.

FIG. 6C similarly shows a central member 3206 having a continuous annular configuration. The central member 3206 includes a plurality of linear posts 3261 extending from the atrial end to the ventricular end and a plurality of zig-zag circumferential members 3266. The ventricular end of the central member 3206 has a smaller diameter (which can be, e.g., 25-30 mm, such as 27 mm) than the diameter of the atrial end (which can be e.g., 30-35 mm, such as 32 mm). Each post 3261 includes a ventricular eyelet or aperture 3236 and an atrial eyelet or aperture 3265. The ventricular apertures 3236 can be configured to connect with apertures 3257 on the strut frame while the atrial apertures 3266 can be configured to connect to apertures 3246 on the anchor assembly 3201. The central member 3206 thus angles inward from the anchor assembly 3201 to the strut frame 3215 so as to connect the two. As shown in FIG. 6A, the central member 3206 can connect the anchor assembly 3201 with the strut frame 3215 and can act as a suspension to allow relative movement between the two.

FIGS. 17A-D show a valve prosthesis 1700 with anchor assembly 1701 that is similar to the prosthesis of FIGS. 6A-6F, but three of the linear posts 1761 of the central member 1706 extend further in the ventricular direction than the rest, and sutures holes on the ovoid leaflet attachment mechanism 1705 are moved further proximally, thereby ensuring that the riveting attachment of the central member 1706 to the strut frame 1715 does not interfere with the attachment of the leaflets to the strut frame 1715.

The expandable anchor, central member or suspension, and strut frame optionally have different spring constants, which is generally a measure of how stiff and strong a material is. For example, the strut frame can have the greatest spring constant, while the central member or suspension can have the lowest spring constant to allow it be deformed most easily. The expandable anchor can have a spring constant in between that of the strut frame and central member. Strut frame can have the greatest spring constant to resist deformation as much as possible.

The central members described herein advantageously prevent or minimize torqueing or twisting of the strut frame in response to torqueing of the expandable anchor. Further, the central member can allow for radial movement while preventing or minimizing axial movement. For example, the elements (e.g., linear posts or individual suspension members) connecting the strut frame to the expandable anchor may have cross sections that are thin in the radial direction and thick in the axial and rotational directions. In some embodiments, the central member can help maintain the axial position of the components (strut frame and anchor) during packaging.

Since there are mitral valve anatomical differences between patients, the central members described herein can allow the prosthesis to be implanted in patients with varying anatomies and accommodate for those differences while preventing the strut frame from deforming too extensively. For example, the mitral valve can be dilated quite extensively in some patients, and thus there may be a desire to have some variability built into the prosthesis. The elements of the central member can compensate for that variability. For example, the same strut frame size can be used with anchors of inner and outer diameters, and the central member can compensate for the dimensional difference. For example, a strut frame having a diameter of 27 mm can be used in an anchor having a diameter of 32-38 mm. Likewise, a strut frame of 29 mm can be used with an anchor have a diameter of 38-44 mm in diameter. The spring length can be increased to support the valve as the anchor diameter increases. Further, the skirt can be configured to cover the gap between the anchor frame and the strut frame.

Figure 18A:
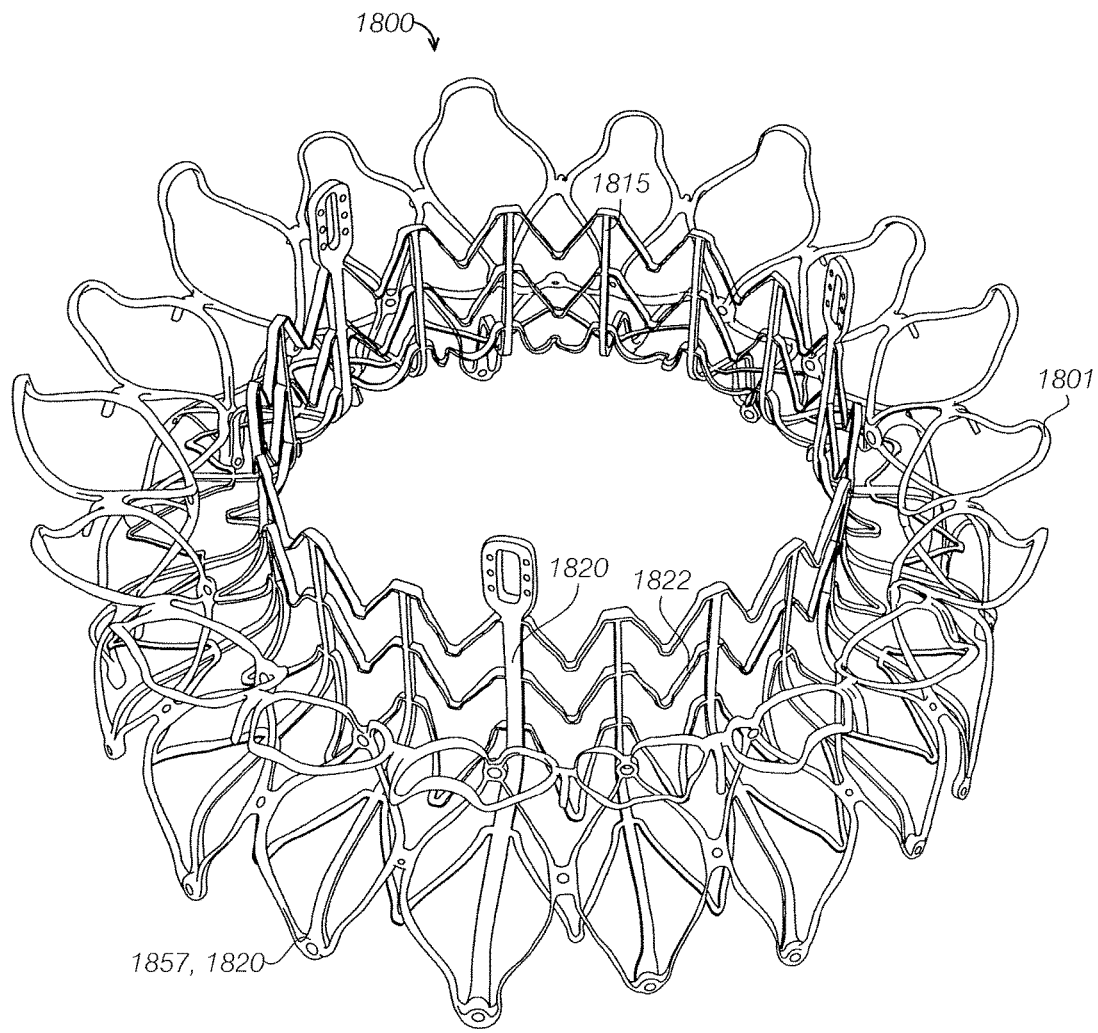
FIG. 18A shows another embodiment of a valve prosthesis.
Figure 18B:
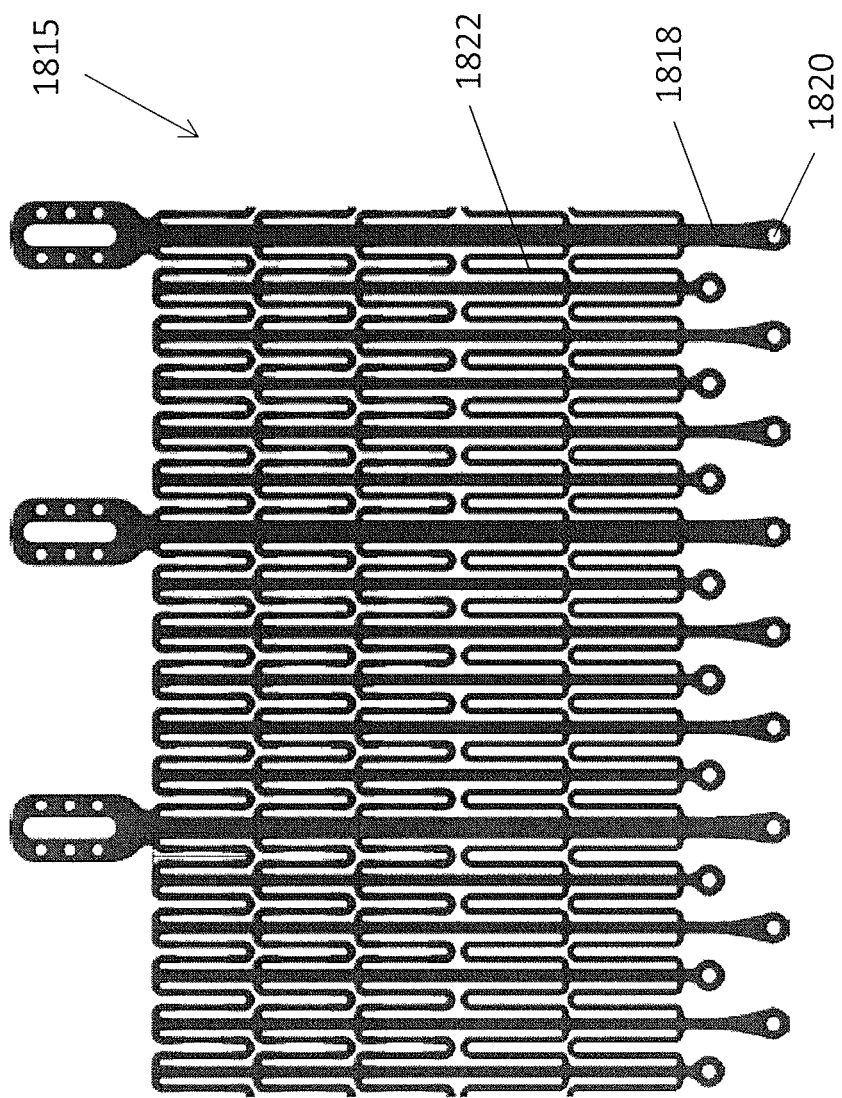
FIG. 18B shows a flattened strut frame of the valve prosthesis of FIG. 18A.
Figure 18C:
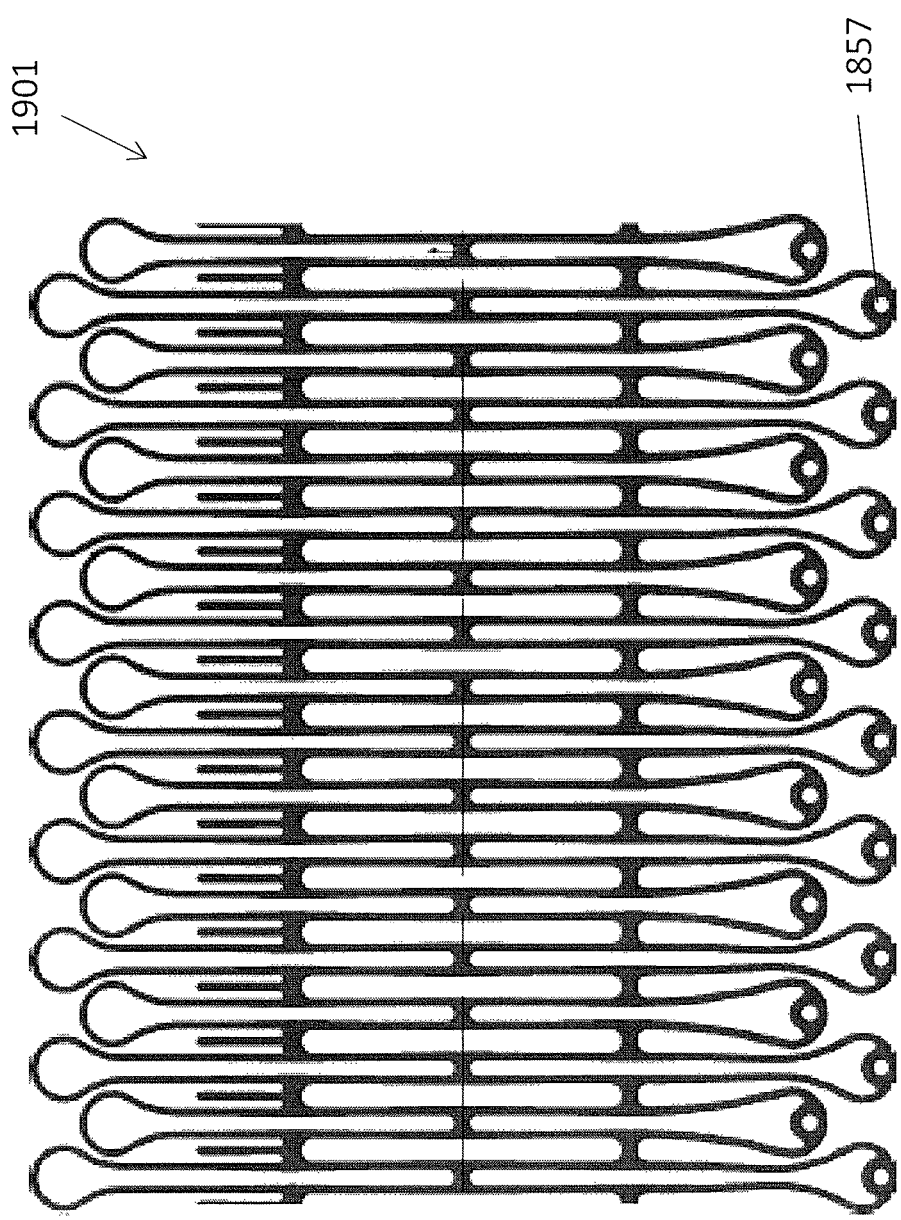
FIG. 18C shows a flattened anchor assembly of the valve prosthesis of FIG. 18A.

In some embodiments, the anchor assembly and/or the strut assembly can have integrated suspension units attached thereto. For example, referring to FIGS. 18A-18C, the valve 1800 includes strut frame 1815 and anchor assembly 1801. As shown in FIGS. 18A and 189B, the linear posts 1818 of the strut frame 1815 extend past the circumferential zig-zag features 1822 of the strut frame 1815 on the atrial side. Further, the posts each include eyelet holes 1820 at the atrial end thereof. The eyelet holes 1820 are configured to line up with eyelet holes 1857 (see FIG. 18C) on the atrial tips of the anchor assembly 1801 to provide for coupling attachment, such as through rivets. The atrial anchor in this embodiment has petals of alternating lengths (as best shown in FIG. 18C), so the extensions of the posts 1818 have alternating lengths to accommodate (as best shown in FIG. 18B). Similar to other embodiments described herein, the atrial side of the strut frame 1806 can flare outwards (see FIG. 18A). The posts 1818 can thus be used to attach the strut frame 1815 to the anchor assembly 1801. Further, because the posts 1801 have extensions in the atrial direction, those extensions can act as springs, such as leaf springs, to provide a suspensions between the main body of the strut frame 1815 and the anchor assembly 1801.

Figure 19A:
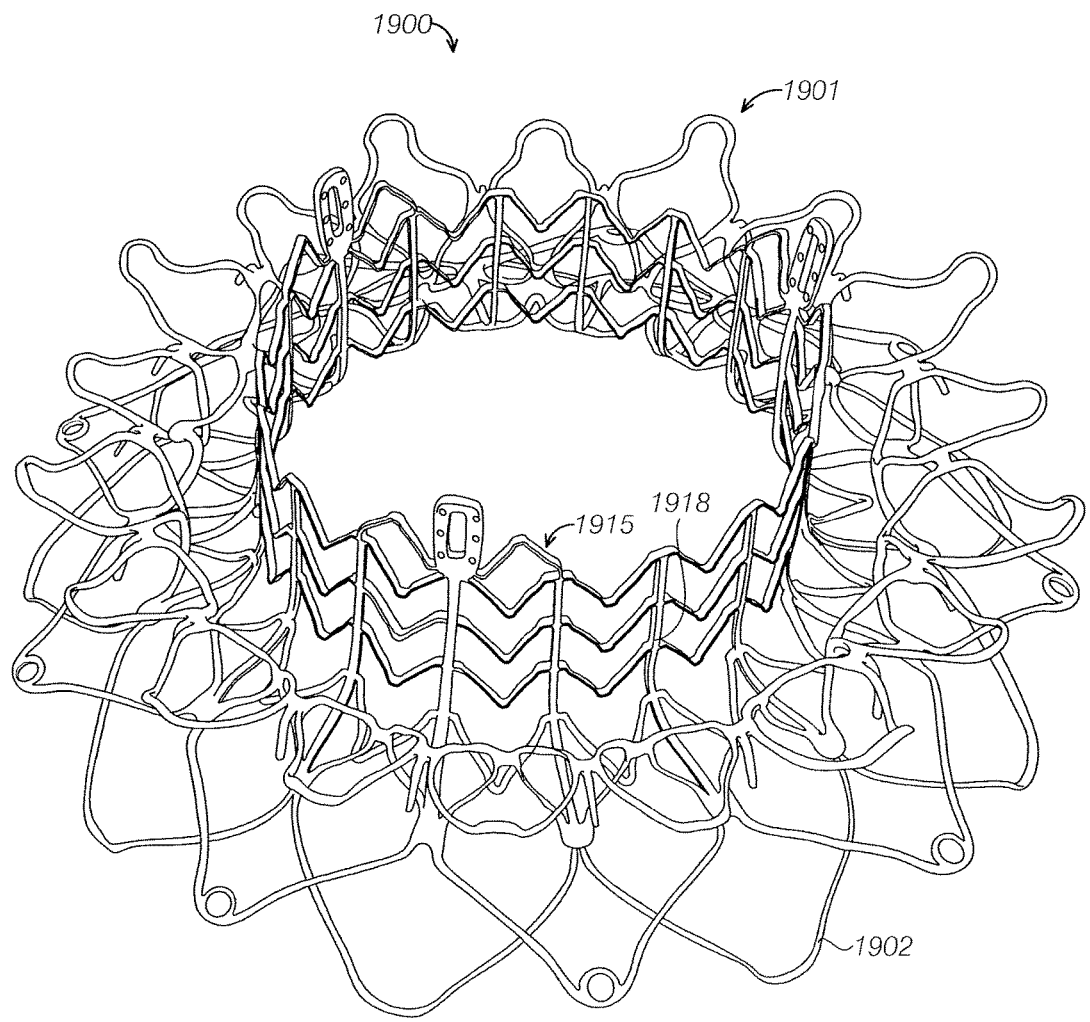
FIGS. 19A-19B shows another embodiment of a valve prosthesis.
Figure 19B:
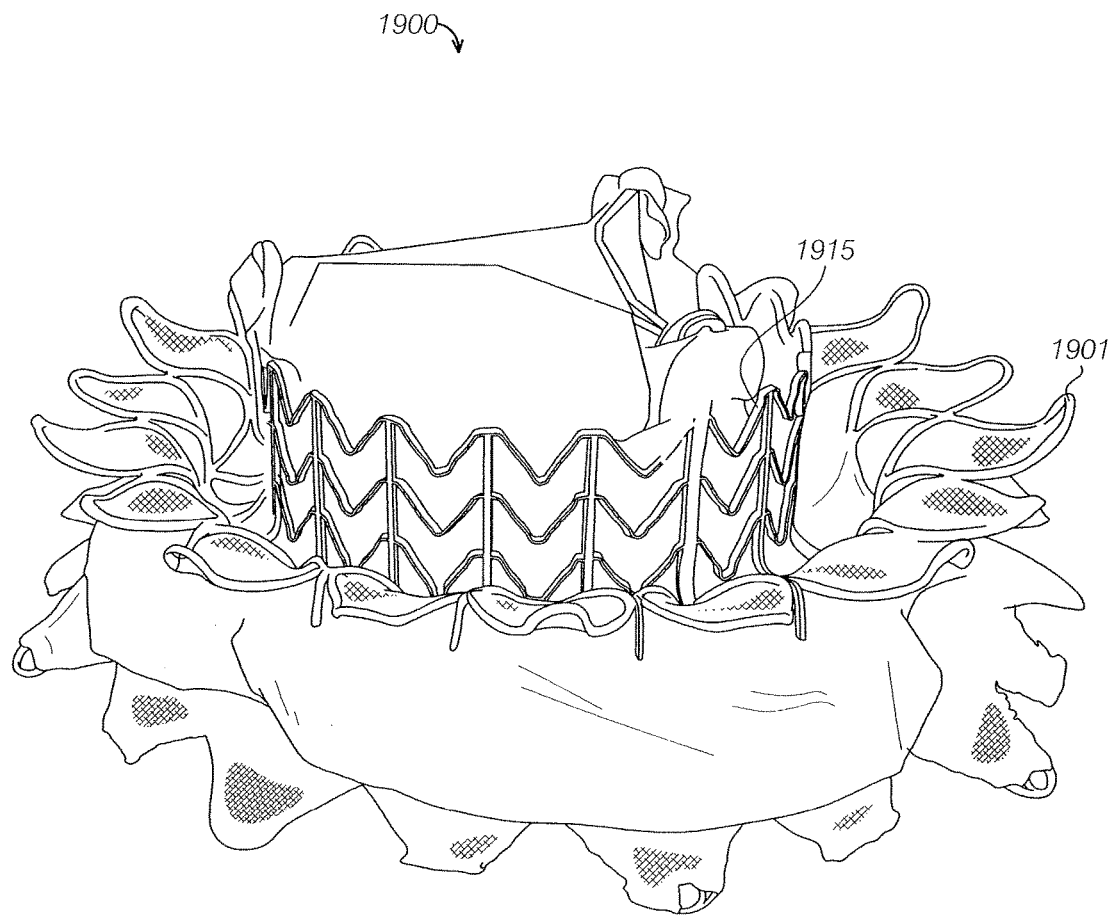
Figure 20A:
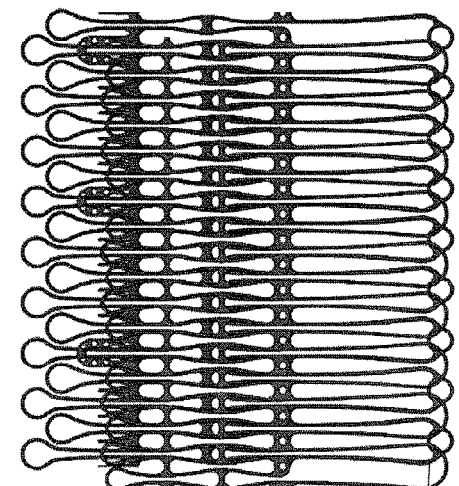
FIG. 20A shows a flattened and overlaid anchor assembly and strut frame.
Figure 20C:
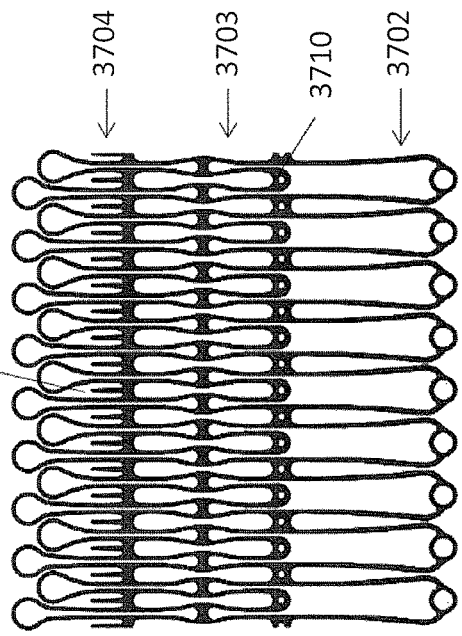
FIG. 20C shows the anchor assembly of FIG. 20A.
Figure 20B:
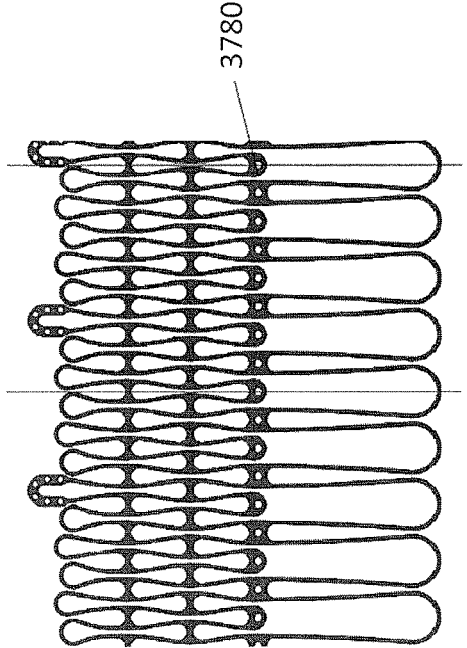
FIG. 20B shows the strut frame of FIG. 20A.

Another example of a valve 1900 with an integrated assembly is shown in FIGS. 19A-19C. In this embodiment, the posts 1918 are attached to the central portion of the anchor assembly 1901 rather than to the atrial petals. Because the posts 1918 are attached to the central portion (thereby providing suspension), the atrial petals of the atrial anchor 1902 can be more flexible, and overlapping petals can be used (as shown in FIG. 19A). Another valve assembly 3700 with the strut frame 3715 attached to the atrial anchor 3703 is shown in FIGS. 20A-20C. That is, the atrial anchor 3702 can include apertures 3710 (see FIG. 20C) configured to attach to apertures 3780 (see FIG. 20B) of the strut frame 3715. The alignment of the anchor 3701 and the strut frame 3715 is shown in FIG. 20A. The valves 1900 and 2700 thus include suspensions characteristics that are provided by offsetting the rivet attachment points towards the atrial side, thereby creating a cantilever beam supporting the leaflet strut coming from the atrium.

Any of the embodiments described hereinabove can further include hooks configured to enhance attachment of the implant to the tissue.

In one embodiment, as shown in FIG. 20C, the hooks 3732 can be positioned in the valleys between extensions 3722 of the ventricular anchor 3704. i.e., can extend from the radial inner-most part of the ventricular anchor 3204. In some embodiments, the hooks 3632 can additionally or alternatively be positioned in the valleys between extensions of the atrial anchor. Advantageously, by placing the hooks in the valley between the extensions, they do not drag on tissue during release and/or repositioning of the device. That is, by being positioned at the inner-most radial position, the hooks will not grab tissue until the atrial and ventricular anchors 3702, 3704 are fully or substantially fully deployed. Moreover, by having the hooks close to the central portion 3603, they will better grab onto meaty tissue of the annulus.

In another embodiment, as shown in FIGS. 6B and 6E, hooks 3232b can extend from the central portion 3203, such as point in radially outwards and/or slightly in the ventricular direction. Hooks 3222a can also extend from the ventricular anchor in the valleys and point substantially in the atrial direction.

The hooks can be configured to embed into annulus tissue, thereby helping to resist the pressure build-up on the ventricular side of the aorta.

When two components are secured together during manufacturing, they are considered to be non-integral, or non-monolithic, components. Different portions of the expandable anchor that are made from the same starting material are considered to be integral, or monolithic. For example, the ventricular anchor, central anchor, and atrial anchor can all be made from the same piece, i.e., be integral with one another. In contrast, a manufacturing step could include cutting a strut and an expandable anchor from different pieces of starting material, and securing them together, and they would be considered non-integral. In some embodiments, when one or more components are secured together, the coupling of the two components can be made so that the two components are rigidly secured at the coupling, or so that the two components can move to some degree at the location of the coupling of the two components (e.g., pivotable).

Rivets as used herein are an example of a coupler, as that term or derivatives thereof is used herein. The locations where components are secured to one another may be referred to as a coupling herein. Coupling also refers to the two components that are secured together. Riveting as used herein is an example of a method that plastically deforms a coupler to secure two or more components together at a coupling.

The rivets can be inserted through the apertures described herein and the ends can then be plastically deformed using known riveting techniques to secure the two or more components together. The rivets can be made of a suitable implantable material, such as platinum, platinum-iridium alloy, tantalum, nickel-titanium alloy, or titanium and titanium alloys, such as titanium 6-4eli. In some embodiments, the riveted coupling can be such that one or more rivets are not tightened all the way down to the secured components, which allows for hinging of the coupling, if desired. Rivets used for hinging may be made of materials suitable for implantable bearing surfaces such as Nitronic 60 alloy, or nitinol. Hinge pins can be coated with low-friction, high-durability coatings, such as diamond-like coating, or titanium nitride.

Use of rivets and hinges (as opposed to, for example, crimp tubes) can provide an additional benefit of preventing cracking that can occur as single pieces of material flex and move. Additionally, rivets and hinges can provide various degrees of relevant movement between portions of the valve, which can allow the valve to be collapsed into a smaller delivery profile for delivery. The relative movement can also provide increased flexibility of the valve during delivery. Rivets can also allow for a variation in the relative orientation of the riveted components. In some embodiments, rivets provide increased flexibility that allows for greater trackability during delivery and better self-centering of the anchor against cardiac tissue (i.e., provides advantages for both access and conformability to the anatomy).

The couplings herein (e.g., riveting) also allow different section of material with different physical properties to be secured to one another. This allows different sections of the expandable anchor to have different properties (e.g., stiffness) than other sections, as may be needed based on, for example, anatomical requirements. For example, atrial anchors can be made thinner than the central portion and/or ventricular anchors.

Coupling and rivets are described further in U.S. patent application Ser. No. 14/677,334, filed Apr. 2, 2015, titled "REPLACEMENT CARDIAC VALVES AND METHODS OF USE AND MANUFACTURE," the entire contents of which are incorporated by reference herein.

Any of the valve prostheses described herein can include a fabric cover and/or skirt or one or more portions of the device. For example, FIG. 6A shows a skirt covering the anchor assembly.

In some embodiments, the valve prostheses have been shown without leaflets for clarity. It is to be understood that each of the embodiments described herein can included replacement leaflets attached thereto.

Any of the valve features or structural details of any device embodiment described herein can be incorporated or combined with any of the other embodiments herein. For example, the central members or suspensions described herein are not limited in use with the expandable anchors and strut frames in the specific embodiment, but can be replaced with any of the features described in any other embodiment.

In use, when the devices described herein can be used as mitral valve replacements. In some embodiments, when the replacement heart valve has been delivered near the mitral valve, the ventricular anchor can be deployed first in a cardiac chamber, such as the ventricle, and retracted to a seated position against the valve orifice, such as the mitral valve orifice. Then the center portion and atrial anchor portion may be deployed in another cardiac chamber, such as the atrium, wherein the expansion and reconfiguration of the atrial anchor and the central portion sandwiches the valve orifice securely between the anchors that have been deployed on either side of the annulus. Other exemplary aspects of the methods of delivery described in U.S. Pat. No. 8,870,948, issued Oct. 28, 2014, and in International Patent Application filed May 13, 2016, titled "CARDIAC VALVE DELIVERY DEVICES AND SYSTEMS," both of which are incorporated by reference in their entireties.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A prosthetic mitral valve comprising:
an anchor assembly having an hour-glass shape an comprising a ventricular anchor configured to sit within a ventricle, an atrial anchor configured to sit within an atrium, and a central portion therebetween, the anchor assembly configured to compress native cardiac tissue at a mitral valve orifice between the ventricular anchor and the atrial anchor;
a plurality of replacement leaflets;
an annular strut frame disposed radially within the anchor assembly, and having a ventricular end and an atrial end, the annular strut frame flared radially outwards at the atrial end relative to the ventricular end; wherein the ventricular end includes a plurality of apertures therein for attachment of the plurality of replacement leaflets thereto; and wherein the atrial end is attached to the anchor assembly such that the entire ventricular end of the annular strut frame is spaced away from the anchor assembly in an inward radial direction.

2. The prosthetic mitral valve of claim 1, wherein the strut frame includes a plurality of arches.

3. The prosthetic mitral valve of claim 1, wherein the atrial end of the annular strut frame is attached to the anchor assembly with a plurality of rivets.

4. The prosthetic mitral valve of claim 1, wherein the prosthetic mitral valve is configured to self-expand from a constrained configuration to an expanded configuration.

5. The prosthetic mitral valve of claim 1, wherein the annular strut frame has a higher spring constant than the anchor assembly.

6. The prosthetic mitral valve of claim 1, wherein the annular strut frame includes a plurality of apertures at the atrial end for connection of the annular strut frame to the anchor assembly.

7. The prosthetic mitral valve of claim 1, wherein the strut frame includes a plurality of linear posts and a plurality of circumferential zig-zag features extending therearound.

8. The prosthetic mitral valve of claim 1, wherein the ventricular end of the strut frame extends axially past the anchor assembly in a ventricular direction.

9. A prosthetic mitral valve comprising:
an anchor assembly having an hour-glass shape and comprising a ventricular anchor configured to sit within a ventricle, an atrial anchor configured to sit within an atrium, and a central portion therebetween;
a plurality of replacement leaflets;
an annular strut frame disposed radially within the anchor assembly, and having a ventricular end and an atrial end, the annular strut frame flared radially outwards at the atrial end relative to the ventricular end; wherein the ventricular end includes a plurality of apertures therein for attachment of the plurality of replacement leaflets thereto; and wherein the atrial end includes a plurality of arches defining peaks extending in an atrial direction and valleys extending in a ventricular direction, wherein one or more peaks of the arches are attached to the anchor assembly such that the entire ventricular end of the annular strut frame is spaced away from the anchor assembly in an inward radial direction.

10. The prosthetic mitral valve of claim 9, wherein the atrial end of the annular strut frame is attached to the anchor assembly with a plurality of rivets.

11. The prosthetic mitral valve of claim 9, wherein the prosthetic mitral valve is configured to self-expand from a constrained configuration to an expanded configuration.

12. The prosthetic mitral valve of claim 9, wherein the annular strut frame has a higher spring constant than the anchor assembly.

13. The prosthetic mitral valve of claim 9, wherein the annular strut frame includes a plurality of apertures at the atrial end for connection of the annular strut frame to the anchor assembly.

14. The prosthetic mitral valve of claim 9, wherein the strut frame includes a plurality of linear posts and a plurality of circumferential zig-zag features extending therearound.

15. The prosthetic mitral valve of claim 9, wherein the ventricular end of the strut frame extends axially past the anchor assembly in a ventricular direction.

16. The prosthetic mitral valve of claim 9, wherein the atrial and ventricular anchors are flared radially outwards relative to the central portion so as to compress native cardiac tissue at a mitral valve orifice between the atrial and ventricular anchors.

* * * * *